(12) United States Patent
Servin

(10) Patent No.: US 9,421,545 B2
(45) Date of Patent: Aug. 23, 2016

(54) SPRING-LESS MULTI-POSITION MICRO-FLUIDIC VALVE ASSEMBLY

(71) Applicant: IDEX Health & Science LLC, Northbrook, IL (US)

(72) Inventor: Carl M. Servin, Rohnert Park, CA (US)

(73) Assignee: IDEX Health & Science LLC, Northbrook, IL (US)

( * ) Notice: Subject to any disclaimer, the term of this patent is extended or adjusted under 35 U.S.C. 154(b) by 0 days.

(21) Appl. No.: 14/861,711

(22) Filed: Sep. 22, 2015

(65) Prior Publication Data

US 2016/0082439 A1  Mar. 24, 2016

Related U.S. Application Data

(60) Provisional application No. 62/054,032, filed on Sep. 23, 2014.

(51) Int. Cl.
| | |
|---|---|
| *B01L 5/00* | (2006.01) |
| *B01L 3/00* | (2006.01) |
| *F16K 99/00* | (2006.01) |
| *F16K 11/074* | (2006.01) |
| *G01N 30/20* | (2006.01) |

(52) U.S. Cl.
CPC ............ *B01L 3/567* (2013.01); *F16K 11/0743* (2013.01); *F16K 99/0003* (2013.01); *F16K 99/0034* (2013.01); *G01N 30/20* (2013.01); *B01L 2200/025* (2013.01); *B01L 2200/027* (2013.01); *B01L 2200/0689* (2013.01); *B01L 2300/12* (2013.01); *B01L 2400/06* (2013.01); *F16K 2099/0084* (2013.01)

(58) Field of Classification Search
CPC ............................ B01L 3/567; B01L 2200/12
See application file for complete search history.

(56) References Cited

U.S. PATENT DOCUMENTS 4,444,066 A  4/1984  Ogle et al.

FOREIGN PATENT DOCUMENTS

| EP | 2708886 | 3/2014 |
|---|---|---|
| GB | 825505 | 12/1959 |
| JP | H01307575 | 12/1919 |
| WO | 2012/151080 | 12/2012 |

OTHER PUBLICATIONS

International Search Report from International Application No. PCT/US2015/051414, mailed Dec. 3, 2015.
Written Opinion from International Application No. PCT/ US2015/051414, mailed Dec. 3, 2015.

*Primary Examiner* — Jyoti Nagpaul
(74) *Attorney, Agent, or Firm* — Beyer Law Group LLP

(57) ABSTRACT

A springless rotary shear that produces compression forces by utilizing the stiffness properties of polymer seals. The valve is designed to produce an effective spring load, with inherent sealing force, by deflecting polymer elements whose response depends on stiffness that is governed by each component's elastic modulus and geometry. A stator seal protrudes thousandths of an inch beyond a stator seal housing. When a stator is fastened down to the stator seal housing the clamping forces are transmitted to the stator seal, rotor seal, shaft adapter, bearings and housings, and the assembly is deflected to a flush position, resulting in a sealing force between the rotor and stator seal. The transmitted sealing force is as a function of the stiffness of each component and the protrusion distance of the stator seal above the mating surface prior to fastening the stator.

13 Claims, 21 Drawing Sheets

SPRING-LESS MULTI-POSITION MICRO-FLUIDIC VALVE ASSEMBLY

RELATED APPLICATIONS

This application claims priority under 35 U.S.C. §119(e) from co-pending U.S. Provisional Patent Application No. 62/054,032, filed Sep. 23, 2014, entitled "SPRING-LESS MULTI-POSITION MICRO-FLUIDIC VALVE ASSEMBLY" which is incorporated by reference in its entirety.

FIELD OF THE INVENTION

The present invention relates to valve assemblies in general, and more particularly to spring-less multi-position valve assemblies for pressurized fluid selection and direction in the field of DNA Sequencing, in-vitro Diagnostics (IVD), HPLC (High Performance Liquid Chromatography) and Analytical instruments.

BACKGROUND OF THE INVENTION

For many years rotary shear valves have been used in pressurized fluid instruments for fluid switching, sample injection, fraction collection, stream sampling, solvent selection and fluid redirection. In the field of HPLC most conventional applications operate in the 1,000 psig to 6,000 psig high pressure domain. Only in the last few years have HPLC pressures increased up to 20,000 psig in order to reduce analysis time and increase performance. By comparison, DNA Sequencing and In-vitro diagnostic instruments in general operate at much lower pressures, from vacuum to positive pressures in the range −10 psig to 200 psig.

With regard to fluid flow control, rotary shear valves are commonly selected for a number of reasons including accuracy, precision, repeatability, reliability, chemical compatibility, ease of automation, relatively long wear and low cost. One of the primary functions of the shear valve is to create a fluidic seal, where leak rate is limited from 0.3 µL/min to 1 µL/min maximum, in order to prevent loss of sample, solvent or other pressurized fluid and achieve precision, accuracy and instrument performance. Of equal importance is the ability to direct fluid from one location to another for sample analysis, solvent selection, purging and other fluidic functions.

The means for creating a nearly leak tight seal is to apply an axial force causing a rotor element and stator element to come into contact by compression. The force created can range from 30 lbf to 800 lbf depending on the application. Most if not all rotary valves apply the compression force by means of springs, such as helical, belleville or clover. Accompanied with these components are additional parts such as washers, adjusting nuts, guides, shims and threaded features. An example of conventional loading methods is found in FIG. 3 of U.S. Pat. No. 8,622,086 where a helical spring is shown contained in an adapter component which rides on ball bearings and also positions and pushes a rotor seal against a stator seal. Another example is described in FIG. 1B of US patent application No. 2014/0191146 showing a conventional method that uses a minimum of 12 parts including 4 springs, 3 washers, spacer, thrust bearing, bearing washers and shims.

Accordingly, it is desirable to provide a low pressure micro-fluidic valve assembly that significantly reduces the part quantity by eliminating a primary element, namely the conventional spring assembly described above.

SUMMARY OF THE INVENTION

The present invention provides a spring-less micro-fluidic valve assembly that includes a stator seal device which defines a substantially planar stator face and an opposite, distal facing stator contact surface perimetrically defined by a contact surface perimeter. The stator seal device includes at least two or more stator channels extending therethrough from the stator contact surface to corresponding stator ports at the stator face. A rotor seal device 22 is also included having a substantially planar rotor face defining one or more rotor channels and an opposite, proximally facing rotor contact surface. The spring-less micro-fluidic valve assembly further includes a relatively rigid actuator housing having an inner wall that defines an axially extending receiving passage therethrough. The inner wall includes a distally facing housing bearing support surface. A shaft adapter is included that is configured for axial receipt in the receiving passage of the actuator housing. The shaft adapter further defines a proximally facing adapter bearing support surface and a distally facing adapter contact surface configured for contact support of the proximally facing rotor contact surface of the rotor seal device. A bearing assembly is disposed between the bearing support surface of the actuator housing and the bearing support surface of the shaft adapter for rotational support of the shaft adapter and rotor seal device thereof about a rotational axis. The spring-less micro-fluidic valve assembly further includes a relatively rigid stator seal housing defining a stator passage formed and dimensioned for axial seated receipt of the stator seal device therein. The seal housing further includes a distally facing seal housing contact surface that defines a receiving port extending into the stator passage. This receiving port is further formed and dimensioned for axial reciprocating receipt of the stator contact surface of the stator seal device therethrough. The stator seal housing includes a proximal portion configured to hard mount to a distal portion of the actuator housing, such that the actuator housing, the bearing assembly, the shaft adapter, the rotor seal device, the rotor seal device and the stator seal housing collectively cooperate to axially position the stator contact surface of the rotor seal device a substantially precise, calibrated distance, δ, beyond the housing contact surface 42 of the stator seal housing 40, in a non-leak-tight condition.

A stator manifold device of the spring-less micro-fluidic valve assembly is configured to mount to the stator seal housing, in a compressed mount condition, such that a distally facing manifold contact surface of the manifold device initially contacts the stator contact surface, in the non-leak-tight condition, and repositions the stator contact surface, to a leak-tight condition, substantially flush with the distally facing housing contact surface of the stator seal housing. In this orientation, the rotor seal device and the rotor seal device collectively being sufficiently compressed together at a compression pressure enabling leak-tight, relatively low pressure fluid flow between corresponding stator ports and at least one rotor channel at the rotor-stator interface therebetween.

Accordingly, an apparatus and method are provided for producing compression forces by simply and efficiently utilizing the stiffness properties of polymer seals. Beginning with the removal of a conventional spring assembly, it follows that ancillary components can also be discarded.

Elimination of parts decreases product cost by reducing component manufacturing expense and inventory.

In one specific embodiment, the stator seal device is comprised of a polymer material, and more particularly, a Polyetherimide (PEI).

In another configurations, the rotor seal device is selected essentially from the group consisting of a polymer, a metallic and a ceramic material. In still another, the stator seal housing and the actuator housing are comprised of a metallic material, such as a electroless nickel plated for corrosion resistance.

Yet another specific embodiment provides that the shaft adapter, the bearing assembly, and the stator manifold device are each comprised of either a metallic material or a polymer material.

Still another specific embodiment provides that the stator seal device further includes a mid section disposed between the stator face and the stator contact surface. The mid section having mid section perimeter wherein at least one portion thereof extends radially beyond that of contact surface perimeter, forming a distal facing stop surface therebetween.

In one arrangement, the calibrated distance, δ, is in the range of about 0.001"+/−0.003" to about 0.015"+/−0.003", and more particularly, in the range of about 0.008"+/−0.003".

The bearing assembly is selected essentially from the group consisting of a ball bearing assembly, a polymetric spherical bearing assembly and a thrust bearing assembly.

In another specific embodiment, the distal facing stator contact surface of the stator seal device and the manifold contact surface are substantially planar and in a leak-tight relationship with one another. Similarly, the adapter contact surface of the shaft adapter and the contact surface of the rotor seal device are substantially planar and in rotationally locked together as a unit.

In still another configuration, an alignment structure cooperatively aligns and rotationally locks the rotor seal device to the shaft adapter. The alignment structure includes two or more corresponding guide pins extend distally from the adapter contact surface, and the contact surface of the rotor device define corresponding recesses for aligned receipt of the guide pins therein.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawings, in which:

DETAILED DESCRIPTION OF THE INVENTION

Figure 1:
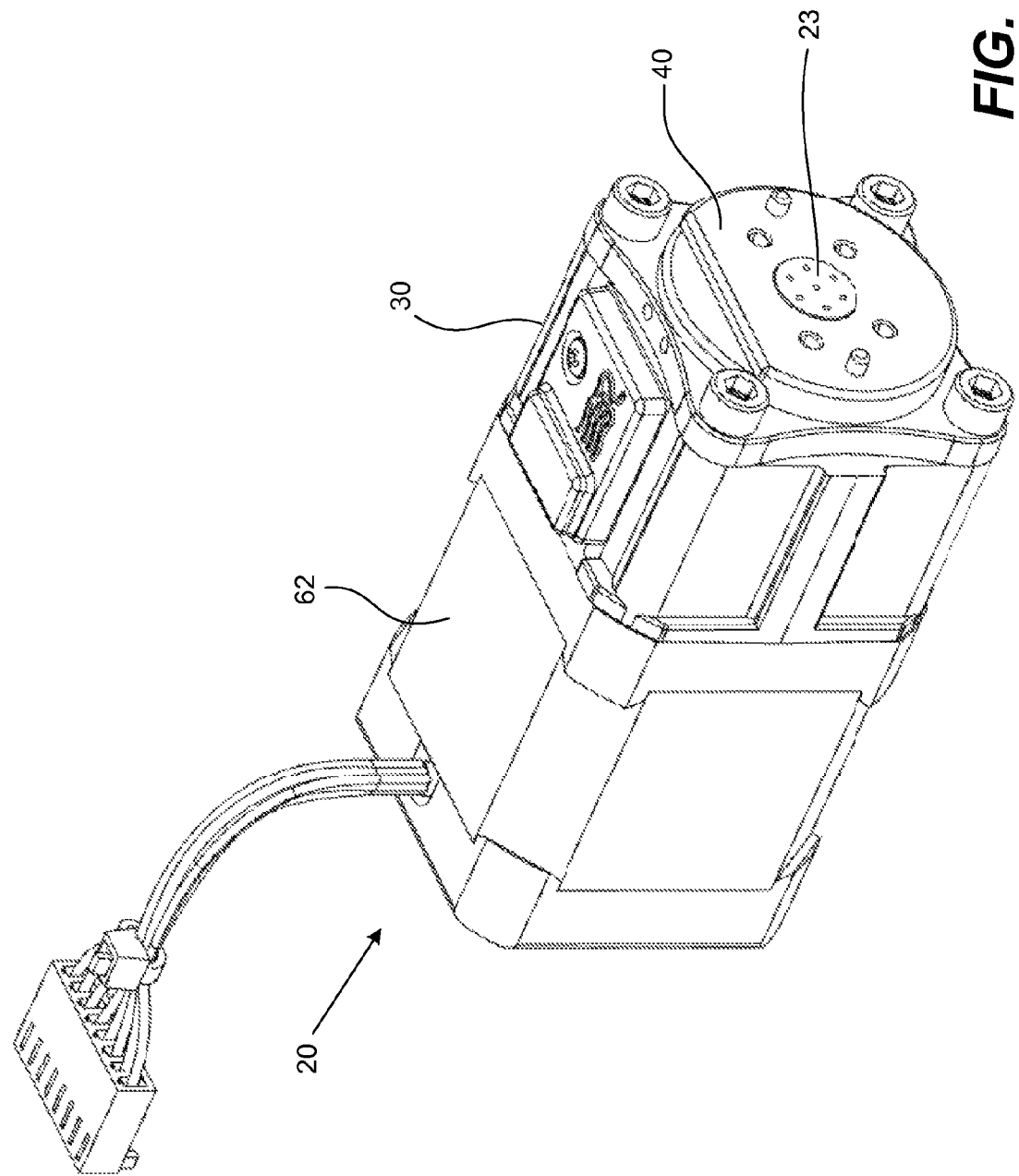
FIG. 1 is a top perspective view of a spring-less micro-fluidic valve assembly, without a stator device mounted thereto, constructed in accordance with the present invention, and shown mounted to a drive motor assembly.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various FIGURES.

Turning now to FIGS. 1-5, a spring-less micro-fluidic valve assembly, generally designated 20, is provided that eliminates conventional compression spring stacks utilized to generate the compression forces necessary to form the leak-tight seal at a rotor/stator interface 21 of a polymer rotor seal device 22 and a polymer stator seal device 23. The spring-less micro-fluidic valve assembly 20 includes the stator seal device 23 which defines a substantially planar stator face 25 and an opposite, distal facing stator contact surface 26 perimetrically defined by a contact surface perimeter. The stator seal device 23 including at least two or more stator channels extending therethrough from the stator contact surface 26 to corresponding stator ports at the stator face 25. The spring-less micro-fluidic valve assembly 20 includes the rotor seal device 22 having a substantially planar rotor face 27 defining one or more rotor channels and an opposite, proximally facing rotor contact surface 28, and a relatively rigid actuator housing 30 having an inner wall 31 defining an axially extending receiving passage 32 therethrough. The inner wall 31 includes a distally facing housing bearing support surface 33.

Figure 3:
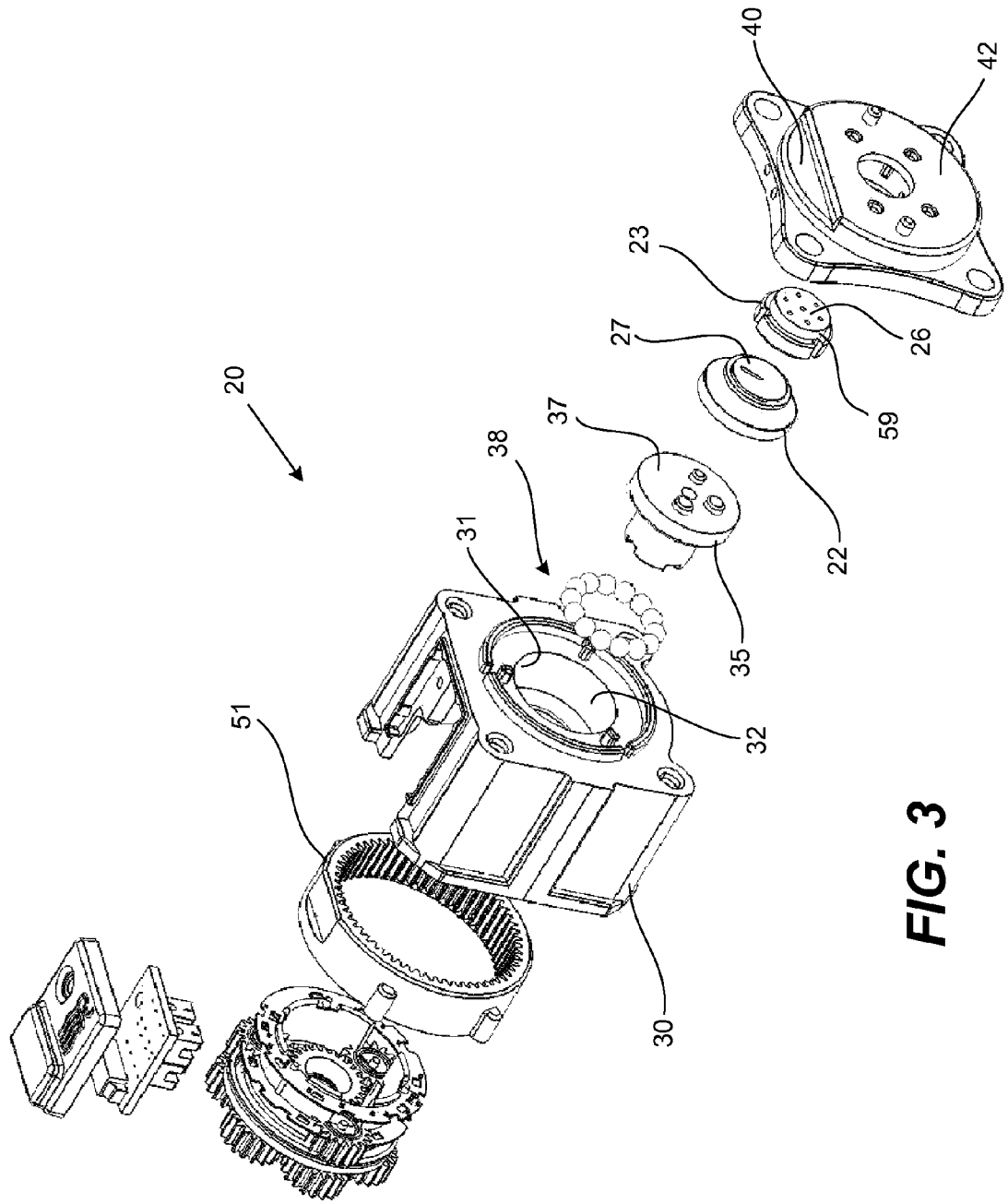
FIG. 3 is an exploded top perspective view of the spring-less micro-fluidic valve assembly of FIG. 1.
Figure 4:
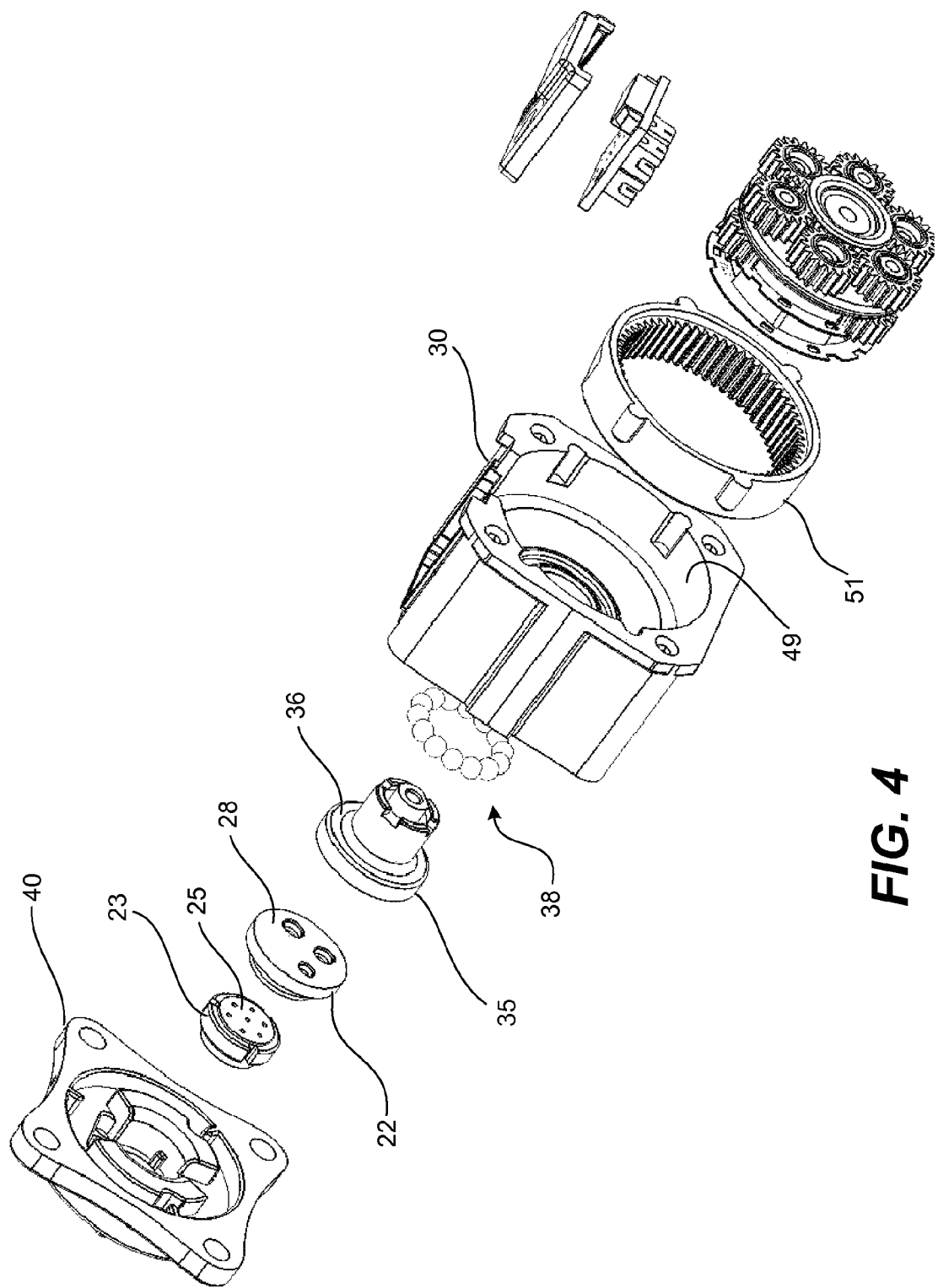
FIG. 4 is an exploded bottom perspective view of the spring-less micro-fluidic valve assembly of FIG. 1.
Figure 5A:
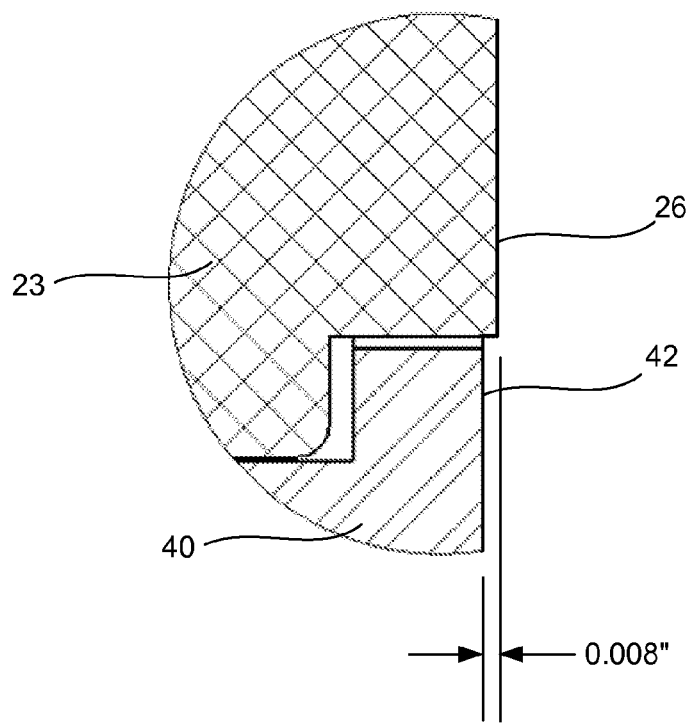
FIG. 5A is a detailed section of a portion of the spring-less micro-fluidic valve assembly taken along the circular line of 5-5 in FIG. 2, in the stator seal's uncompressed state.

FIG. 3 best illustrates that a shaft adapter 35 is included that is configured for axial receipt in the receiving passage 32 of the actuator housing 30. The shaft adapter 35 further defines a proximally facing adapter bearing support surface 36 and a distally facing adapter contact surface 37 configured for contact support of the proximally facing rotor contact surface 28 of the rotor seal device 22. A bearing assembly 38 is disposed between the bearing support surface 33 of the actuator housing 30 and the bearing support surface 36 of the shaft adapter 35 for rotational support of the shaft adapter 35 and rotor seal device 22 thereof about a rotational axis. The spring-less micro-fluidic valve assembly 20 further includes a relatively rigid stator seal housing 40 defining a stator passage 41 formed and dimensioned for axial seated receipt of the stator seal device 23 therein, and a distally facing seal housing contact surface 42 that defines a receiving port 43 extending into the stator passage 41. This receiving port 43 is further formed and dimensioned for axial reciprocating receipt of the stator contact surface 26 of the stator seal device 23 therethrough. The stator seal housing 40 includes a proximal portion configured to hard mount to a distal portion of the actuator housing 30, such that the actuator housing, the bearing assembly 38, the shaft adapter 35, the rotor seal device 22, the rotor seal device 23 and the stator seal housing 40 collectively cooperate to axially position the stator contact surface 26 of the rotor seal device 23 a substantially precise, calibrated distance, δ, beyond the housing contact surface 42 of the stator seal housing 40, in a non-leak-tight condition (FIGS. 1 and 5A).

Finally, a stator manifold device 45 is configured to mount to the stator seal housing 40, in a compressed mount condition (FIGS. 2 and 5B), such that a distally facing manifold contact surface 46 of the manifold device 45 initially contacts the stator contact surface 26, in the non-leak-tight condition, and repositions the stator contact surface 26, to a leak-tight condition (FIG. 5B), substantially flush with the distally facing housing contact surface 42 of the stator seal housing 40. In this orientation, the rotor seal device 23 and the rotor seal device 22 collectively being sufficiently compressed together at a compression pressure enabling leak-tight, relatively low pressure fluid flow between corresponding stator ports and at least one rotor channel at the rotor-stator interface 21 therebetween.

Accordingly, a sufficient degree of compression forces are generated between the stator seal and the rotor seal by simply and efficiently utilizing the stiffness properties of polymer seals. For low fluid pressure situations, this axial compressive pressure enables the removal of conventional spring stack that are widely applied, as well as an ancillary components that are used therewith. Such an elimination of parts decreases product cost by reducing component manufacturing expense and inventory. In addition, fewer parts typically lead to an increase in product reliability and performance. Finally, given the direction technology is driven in terms of smaller and more compact designs, it will be understood how the present invention enables significant reduction of the overall valve size which contributes to a likewise beneficial reduction in instrument size and cost.

The present invention is particularly suitable for lower pressure applications, such as DNA Sequencing and In Vitro Diagnostics, and operating at fluid pressures operating in the range of about −10 psi to about 200 psi. For these applications, the generated compression forces at the rotor/stator interface 21 should be in the range of about 500 psi to about 1500 psi.

The operation of the present invention depends on the stiffness characteristics of the components under compression. Stiffness, K, is defined as the rigidity of an object and resistance to deformation. All materials, whether metals, plastics or elastomers have a property called stiffness. In general, K is a constant dependent upon geometric factors of the object such as Cross-sectional Area, A, Thickness, t, and the Elastic Modulus, E. The formula for stiffness is:

$$K=E*A/t. \qquad [1]$$

In addition stiffness can be defined as:

$$K=F/\delta \qquad [2]$$

where F is the force applied to the component and δ is the displacement produced by the force. Force F is of particular importance to the present invention and can be easily derived from equation [2] giving:

$$F=K*\delta. \qquad [3]$$

Therefore, effective spring load, with inherent sealing force, is produced by deflection of polymer elements and depends on stiffness that is governed by each component's elastic modulus and geometry. In addition, since stiffness may not be linear for some materials, the amount of deflection will affect its value and consequently affect the effective spring load.

These equations are of course a simplification of more complex mathematical models that predict how an object will deform, especially in the case of polymers where strain under load, which is not linear, will occur in more than one direction and depend on how the object is constrained. However, if strain is limited to the elastic range of the material and forces are applied in only one direction, it has been observed that linear formula combined with empirical data are sufficient and effective for estimating how an object or assembly of components deflects under an axially applied load, or for estimating the resultant load given a defined deformation. Since deflection of the component must be relatively small, so as to prevent plastic deformation which causes unpredictable change in shape over time, it is therefore necessary to design components with critical features having tolerances in the range of about +/−0.001".

Figure 2:
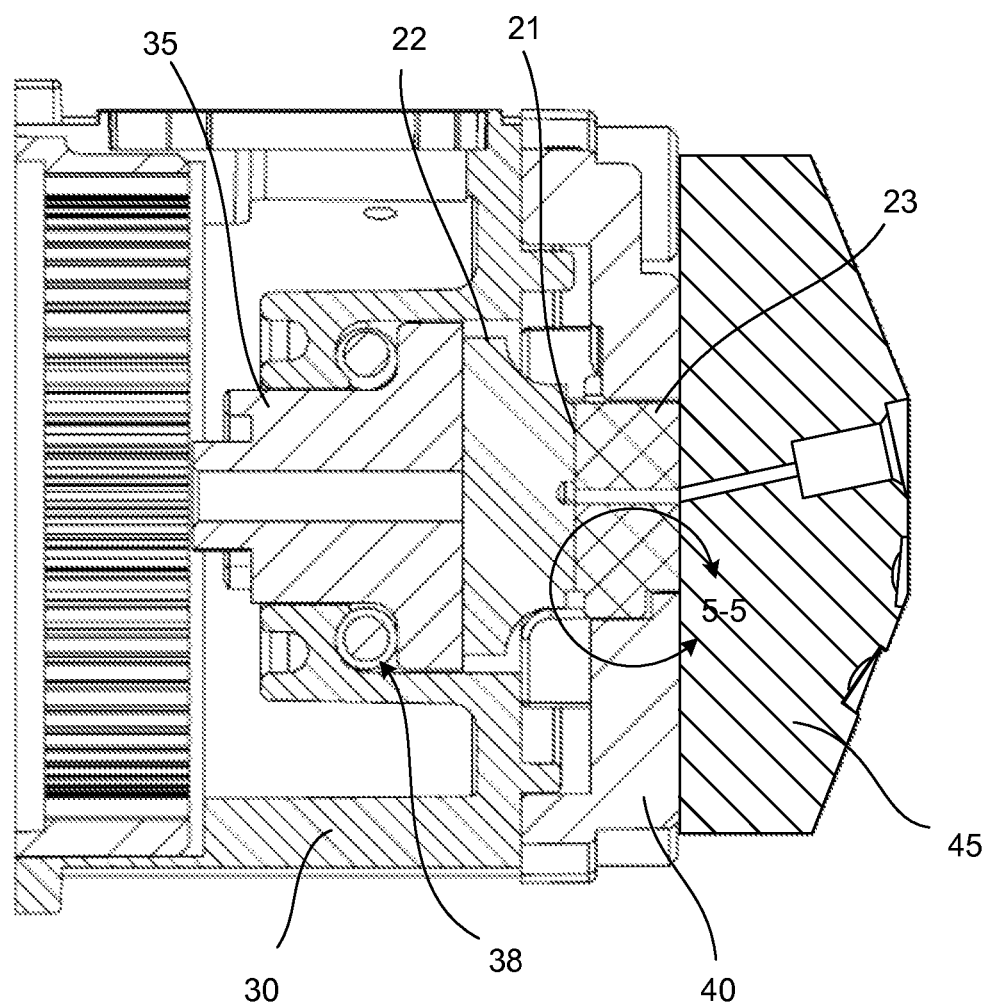
FIG. 2 is a side elevation view, in cross section, of the spring-less micro-fluidic valve assembly of FIG. 1.

In accordance with the present invention, as shown in FIGS. 1 and 2, a full valve assembly 20 is provided with a size seventeen (17) motor 62. As mentioned above, the valve assembly 20 includes two primary components, a polymer rotor seal device 22 and polymer stator seal device 23. These seals are selected of a material with known physical properties, which are designed to be accurately compressed (deflected) a designed amount. Hence, upon assembly of the valve assembly 20, the requisite axial compression force between the rotor seal device 22 and the stator seal device 23 is generated, forming a fluid-tight seal at the rotor/stator interface 21.

Briefly, referring back to FIGS. 1-4, the rotor seal device 22 is supported by a shaft adapter 28 which sits atop the bearing assembly 38. In this specific embodiment, the bearing assembly 38 is provided by ball bearings that are supported between the bearing support surface 33 (e.g., a bearing race) of the actuator housing 30 and the bearing support surface 36 of the shaft adapter 28. When the stator manifold device 45 is mounted to the stator seal housing 40, the manifold contact surface 46 of the manifold device contact the stator contact face 26 of the stator seal device 23, compressing the stator seal device against the rotor seal device 22 (i.e., the compressed mount condition of FIGS. 2 and 5B).

In one specific example of the present invention, the shaft adapter 28 is comprised of unfilled nylon, the rotor seal device 22 is comprised of PolyChloro-TriFluoro-Ethylene (PCTFE), the stator face 25 is composed of Ultra H-high Molecular Weight PolyEthylene (UHMWPE) while the stator manifold device 45 material is ULTEM® Polyetherimide. The stator manifold device 45 can be a stand-alone component with ports for direct application of input and output lines or it can be a manifold to which are assembled a variety of parts including pump and liquid sensor with a variety of port and channel configurations and capable of mounting to an analytical instrument.

Figure 5B:
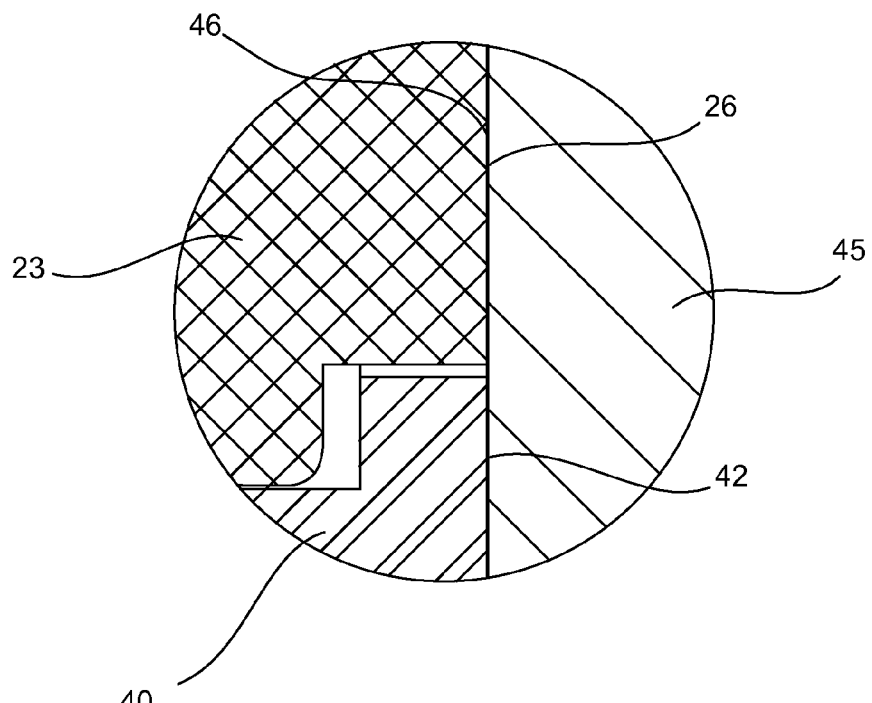
FIG. 5B is a detailed section of a portion of the spring-less micro-fluidic valve assembly taken along the circular line of 5-5 in FIG. 2, in the stator seal's compressed state.

FIG. 5A best illustrates a closer view of the stator seal device 23 where the corresponding substantially planar contact surface 26 is protruding above the mating surface of the stator seal housing 40. This particular embodiment has contact surface 26 protruding (i.e., the calibrated distance, δ) about 0.008"+/−0.003". beyond the seal housing contact surface 42 of the stator seal housing 40, although the range of protrusion without significant plastic deformation is a range of about 0.001"+/−0.003" to about 0.015"+/−0.003". When the stator manifold device 45 is fastened down to the stator seal housing 40 (as shown in FIG. 2), the clamping forces are transmitted to the stator seal device 23, rotor seal device 22, shaft adapter 28, bearings 38 and housings 30 and 40. Consequently, the assembly is deflected 0.008" to a flush position (i.e., the substantially planar contact surface 26 being deflected flush with the substantially planar seal housing contact surface 42, as shown in FIG. 5B), resulting in a sealing force between the rotor seal device 22 and stator seal 23 at the rotor/seal interface 21 (FIG. 2). The transmitted sealing force is a function of the stiffness of each component and the initial distance above flush (protrusion of the stator seal above the mating surface prior to fastening the stator).

With the aid of a compression test instrument, such as the INSTRON® Compression Tester, the stiffness of components and sub-assemblies can be determined for the purpose of initial estimation and to derive final valve load-deflection relationships. In one particular example, the average stiffness of the sub-assembly comprised of the actuator housing 30, ball bearings 38, and shaft adapter in the present invention was measured to be K=96.7 k lb/in. Separately, the average stiffness of the PCTFE rotor seal device 22 and UHMWPE stator seal device 23 were measured to be about 148 k lb/in and about 37 k lb/in, respectively. Therefore, the equation for the valve assembly stiffness is 1/K=1/96.7 k+1/148 k+1/37 k equating to a total sub-assembly stiffness of K=22.7 k lb/in.

Using the INSTRON® tester for analyzing the assembled valve results in a measurement of about 22.9 k lb/in in the range about 0.005" to 0.011", which confirms the accuracy of individual measurements. Based on an assembly stiffness of about 22.9 k lb/in, the resulting sealing force can range from about 114 lbf to about 252 lbf for a deflection of about 0.008+/−0.003 inches. It is interesting to note that the calculated valve stiffness is 32 k lb/in, obtained using the equation[1] K=E*A/t, giving a 40% error above the measured stiffness. Although general material property data and simplification of geometric parameters are sufficient for initial estimation, the most effective design will rely on empirical data both for accuracy and for a better understanding of the load-deflection relationship to prevent operating in the plastic deformation region.

In one example of the present invention, typical materials used for the polymer seals in low pressure applications will have a tensile strength ranging from about 3,000 psi to about 10,000 psi, and an elastic modulus ranging from about 100,000 psi to about 200,000 psi. For high pressure applications, in another example, the polymer tensile strength can reach up to about 25,000 psi with elastic modulus up to about $1 \times 10^6$ psi.

It has been observed that an important parameter for a repeatable and robust design is to control tolerances. If the tolerances are too wide, then on the lower end of the tolerance band, there will be no material to deflect. On the upper end of the tolerance band, when the tolerances are too wide, too much strain can result in poor performance. Excessive deflection of polymer materials, for instance, can cause plastic deformation, resulting in a loss of sealing force, and even stress failure.

In the present invention, the calibrated distance, δ, the stator seal contact surface 26 sits above the housing contact surface 42 prior to fastening the stator is calculated to be about 0.008" with an RSS (root sum square) tolerance of +/−0.003". Polymer seal thickness tolerances are tightly controlled through proprietary lapping and polishing processes, resulting in tolerances in the range of about +/−0.001 inches. Other critical dimension tolerances in the actuator housing 30 and stator seal housing 40 are easily controlled by standard machining practices. Manufacturing cost, moreover, is kept at a minimum by die casting metal parts, secondary machining operations and injection molding plastics.

Figure 6:
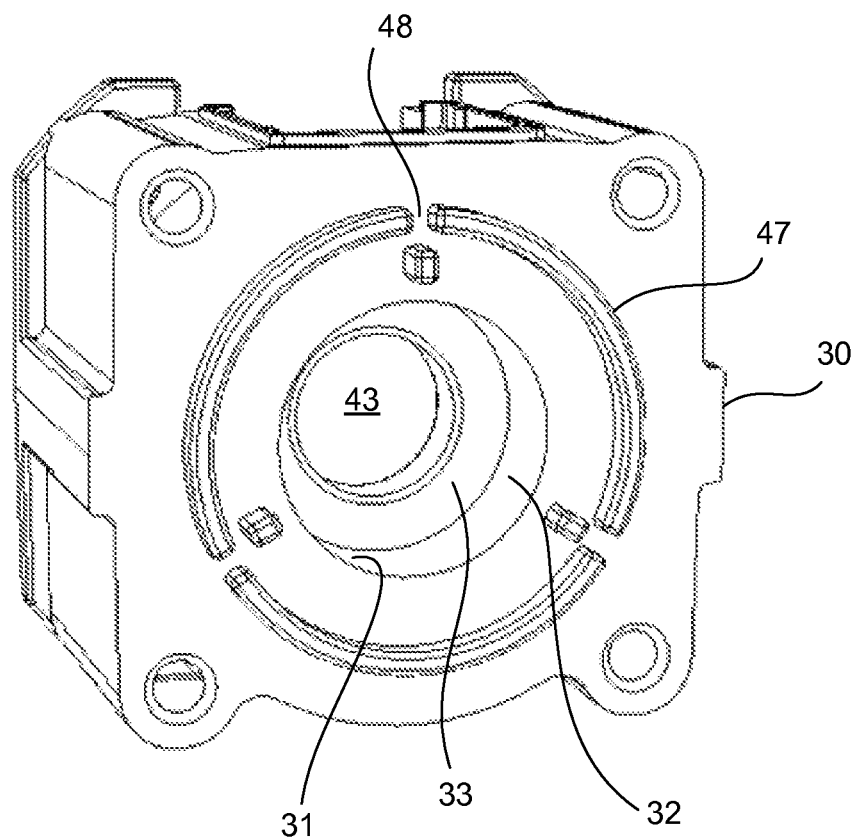
FIG. 6 is an enlarged, front perspective view of an actuator housing of the spring-less micro-fluidic valve assembly of FIG. 3.

FIG. 6 represents topside the die cast actuator housing 30 which includes multiple arc segments 47 with an outside diameter wall tightly toleranced to align with a receiving wall 44 of the stator seal housing 40. In addition, clocking or angular alignment and positioning of the stator seal housing 40 is accomplished using three slots 48 between the arc segments 47 of the housing 30. The actuator housing 30 features a ball bearing race (housing bearing support surface) 33 for a quantity of fourteen (in this example) steel ball bearings of the bearing assembly 38. The actuator housing is preferably electroless nickel plated for corrosion resistance and to provide a hard, durable wear surface for the steel ball bearings.

Figure 7:
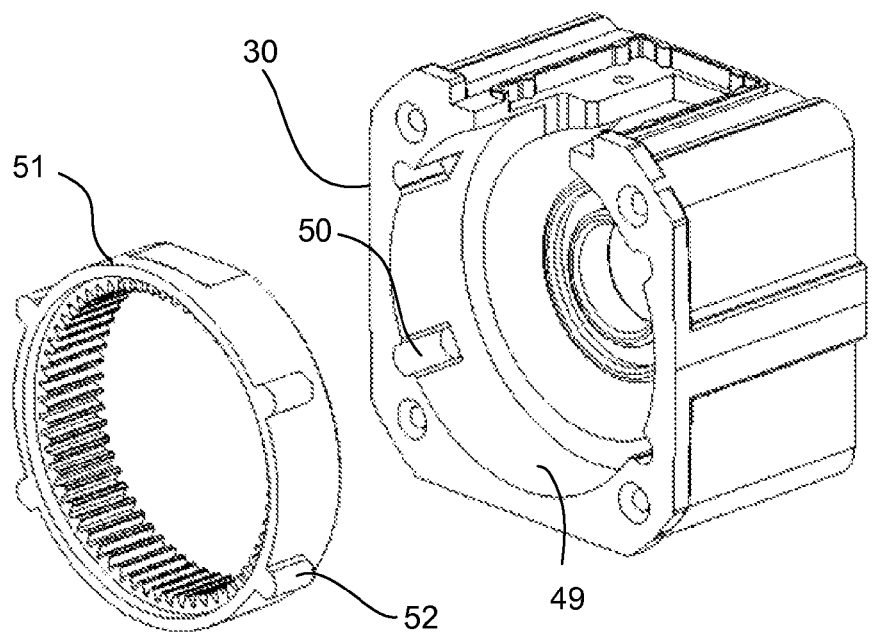
FIG. 7 is an exploded rear perspective view of the actuator housing of FIG. 5 with a ring gear prior to installation.
Figure 8:
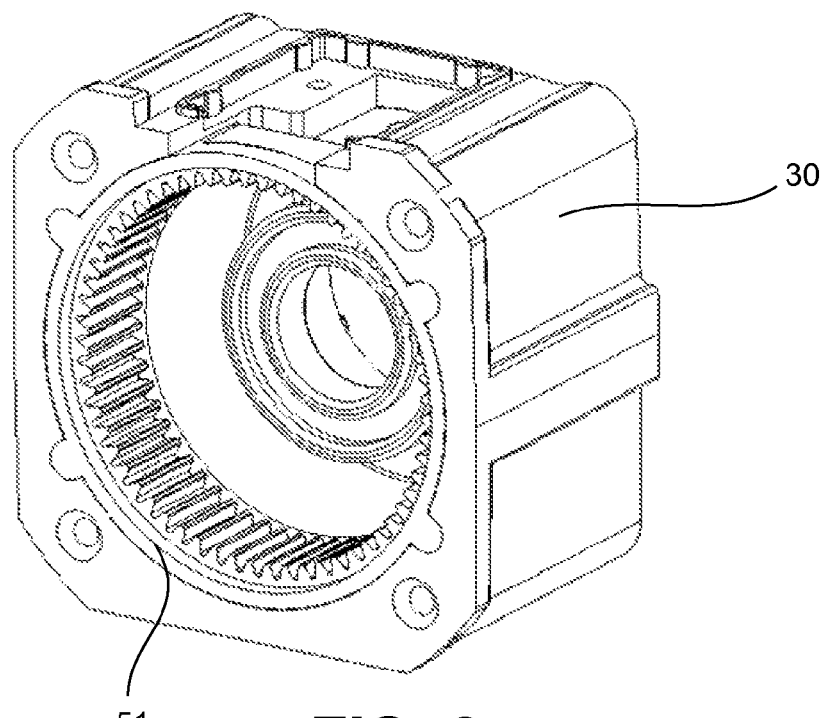
FIG. 8 is a rear perspective view of the actuator housing of FIG. 6 with the ring gear installed.

The back side of the actuator housing 30, as shown in FIG. 7, and an inner wall 49 having a diameter configured for receipt of a pressed-in injection molded ring gear 51. The housing further includes four housing slots 50 which are sized for axial sliding receipt four alignment ring gear ribs 52 of the actuator housing 30, as shown in FIG. 8.

Figure 9:
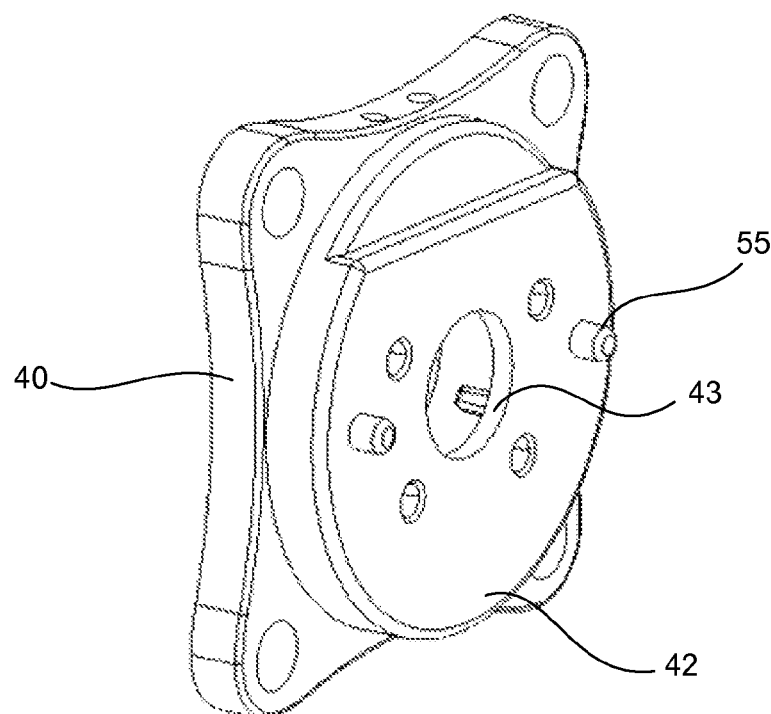
FIG. 9 is an enlarged, front perspective view of a stator seal housing of the spring-less micro-fluidic valve assembly of FIG. 3.

Turning now to FIG. 9, the stator seal housing 40 front side is shown which includes cast-in alignment pins 55 protruding distally from the housing contact surface 42 of the stator seal housing 40. These pins 55 enable positioning, alignment and mounting support for the contact surface 46 of the stator manifold device 45. For the easy for fabrication, both the housing contact surface 42 and the manifold contact surface 46 are substantially planar, as is the stator contact surface.

Figure 10:
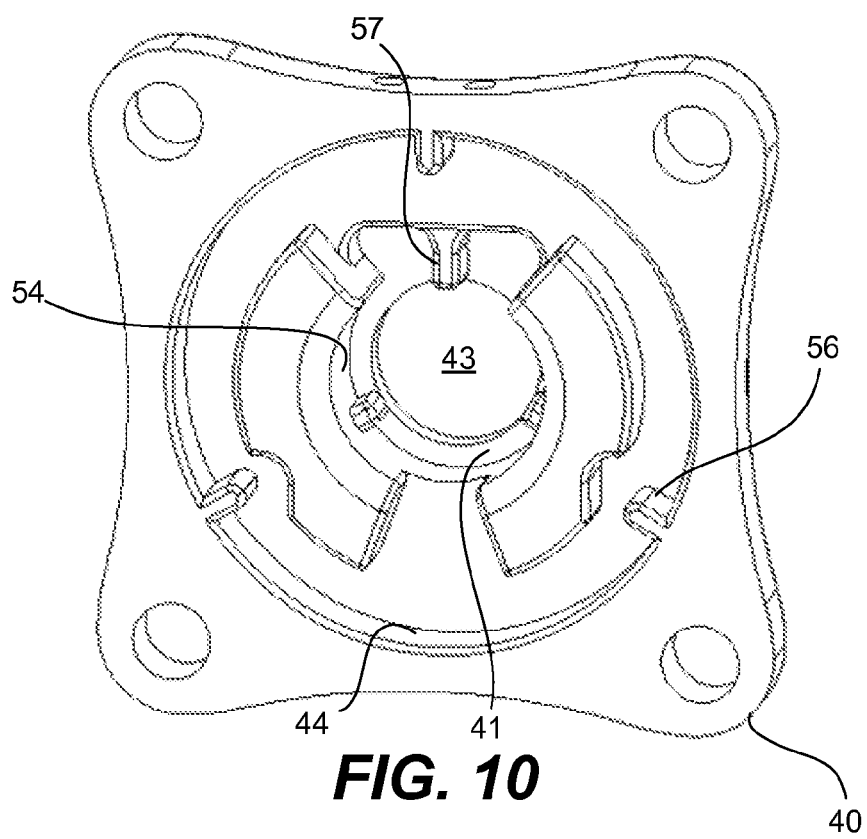
FIG. 10 is a rear perspective view of the stator seal housing of FIG. 9.

The stator seal housing 40 back side (FIG. 10) includes the tightly tolerance inside wall 44, and three alignment ribs 56 protruding radially inward therefrom for engaging the arc segments 47 of the actuator housing 30. In addition, an interior wall 54, that defines a portion of the stator passage 41, further includes three positioning ribs 57 formed and dimensioned to position and align the stator contact surface 26 through the receiving port 43 of the stator seal housing 40. The entire die cast part is electroless nickel plated for corrosion resistance.

Finally, the interior walls defining the receiving port 43 of the stator seal housing 40 are relatively tightly tolerance d for reciprocating receipt to the contact surface perimeter of the nipple portion 59 of the stator seal device 23. However, the interior wall of the receiving port 43, and the outer wall of the contact surface perimeter must be sized to enable axial movement of the nipple portion 59 during compression of the stator device 23. Hence, some diametric expansion during the compression must be take into account.

Figure 11:
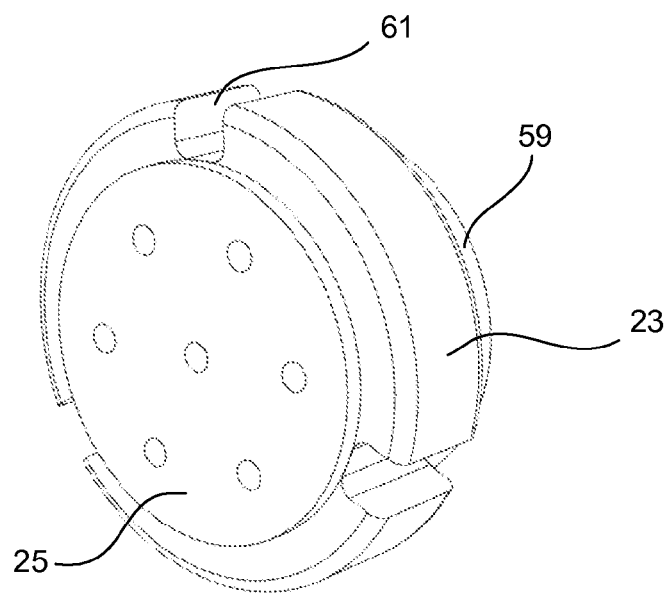
FIG. 11 is an enlarged, front perspective view of a stator seal of the spring-less micro-fluidic valve assembly of FIG. 3.
Figure 12:
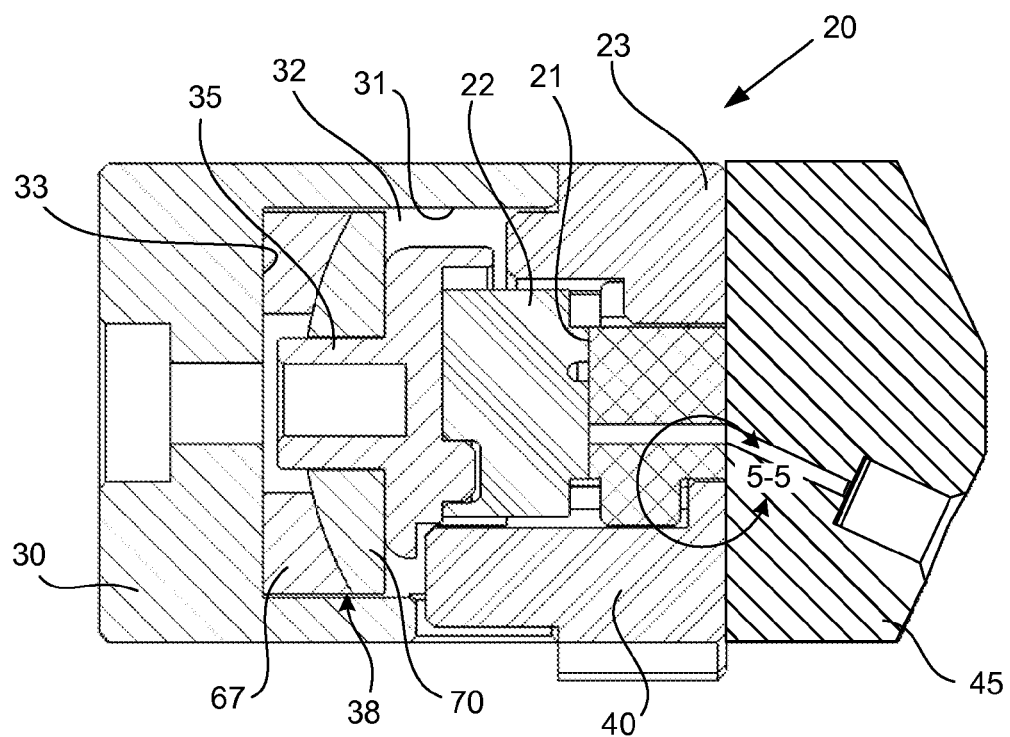
FIG. 12 is a side elevation view, in cross section, of an alternative embodiment of the spring-less micro-fluidic valve assembly of FIG. 1, having a spherical bearing.

FIG. 11 depicts the stator face 25 of stator seal device 23. Alignment slots 61 are provided for the corresponding positioning ribs 57 when seated in the stator passage of the stator seal housing 40. The midsection of the stator seal device 23 is diametrically wider than that of the outer wall of the nipple portion 59, at least at portions, forming a circular shoulder with a distal facing stop surface 63. This shoulder enables the accommodation of the slots 61, as well as limiting the distal travel of the nipple portion through the receiving port 43.

In one alternative embodiment of the present invention, as shown in FIGS. 12-15, the valve assembly 20 similarly consists of a polymer rotor seal device 22 and polymer stator seal device 23. The rotor seal device 22 is rotatably supported by a shaft adapter 28 which sits atop the bearing assembly 38. In this alternative configuration, the bearing assembly is provided by a two-part spherical thrust bearing 38 contained in receiving passage 32 of the actuator housing 30. Both the inner wall 31 and housing bearing support surface 33 provide rotational support to the shaft adapter 28, and thus, and the rotor seal device 22. Briefly, s shown in FIGS. 14 and 15, the two-part spherical thrust bearing 38 includes a base portion 67 and a spherical washer 70.

Similarly, a stator manifold device 45 is mounted to the stator seal housing 40 and contacts the contact surface 26 of the stator seal device 23, compressing the sub-assembly together, in the same manner as previously described in FIGS. 5A to 5B.

In this specific alternative embodiment of FIGS. 12-15, the shaft adapter 28 is made from aluminum or steel, the rotor seal device 22 material is PCTFE, the stator face seal 23 is UHMWPE while the stator manifold device 45 material is ULTEM®. The stator manifold device 45 can be a stand-alone component with ports for direct application of input and output lines or it can be a manifold to which are assembled a variety of parts including pump and liquid sensor with a variety of port and channel configurations and capable of mounting to an analytical instrument. FIGS. 5A and 5B, applies to this design variation just as the initial embodiment where the contact surface 26 of the stator seal device 23 protrudes thousandths of an inch beyond the seal housing contact surface 42 of the stator seal housing 40.

Figure 13:
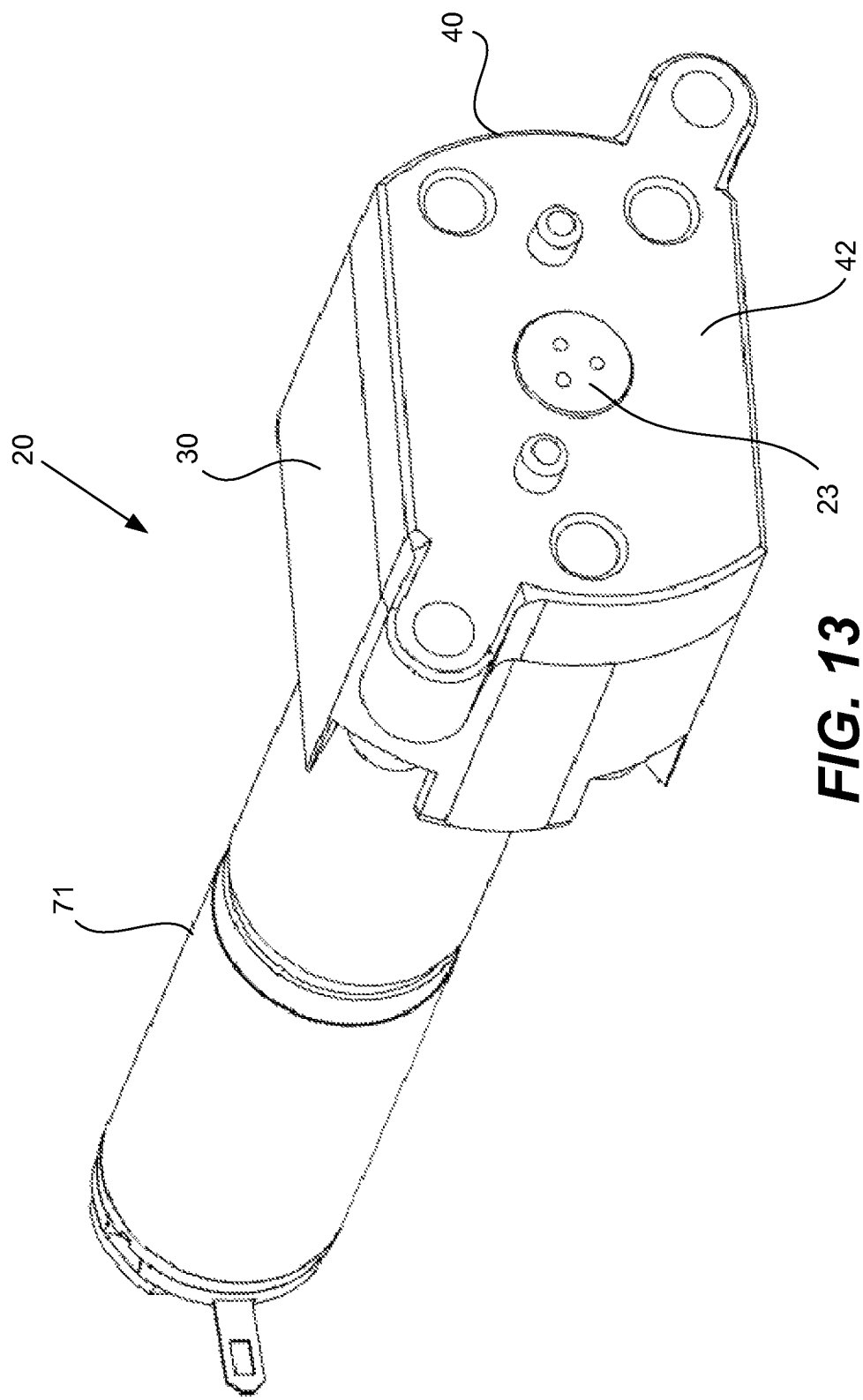
FIG. 13 is a front perspective view of the alternative embodiment spring-less micro-fluidic valve assembly of FIG. 12, without a stator device mounted thereto and shown mounted to a drive motor assembly.
Figure 18:
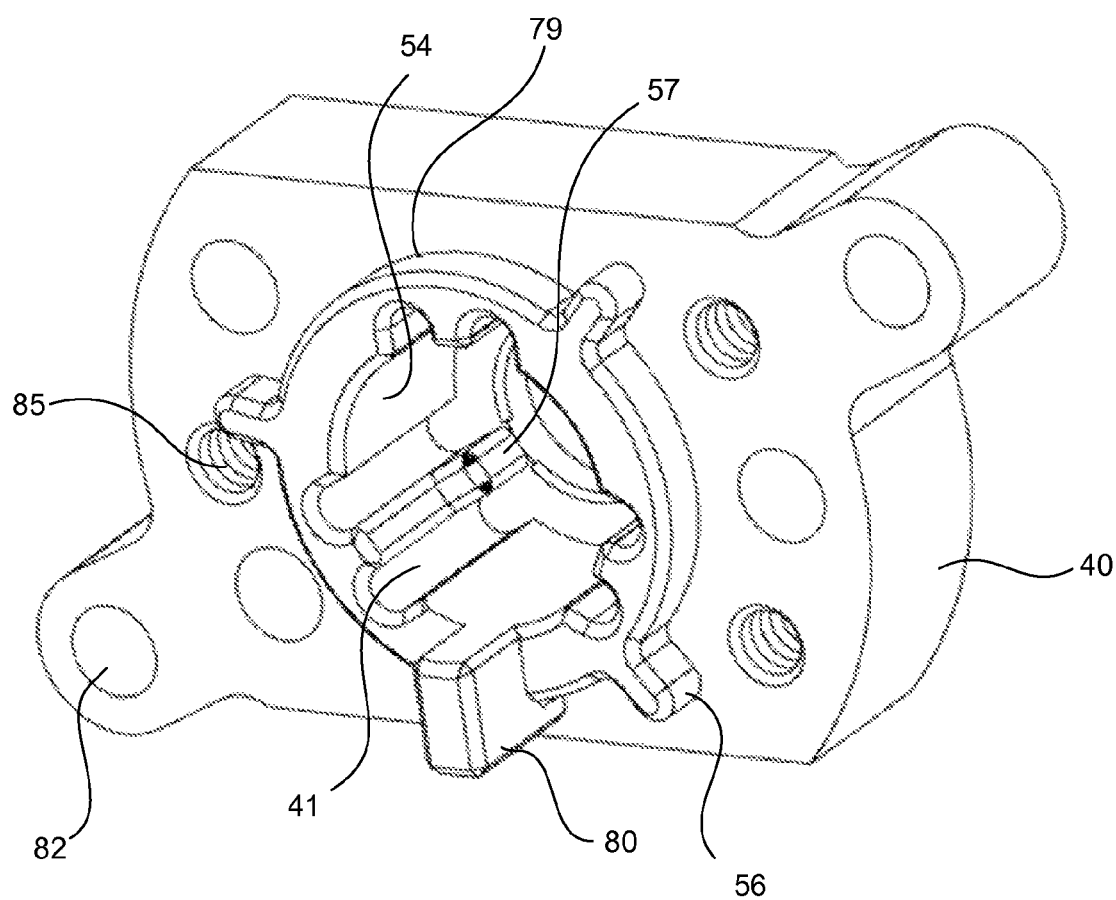
FIG. 18 is a rear perspective view of the stator seal housing of FIG. 17.

FIG. 13 best illustrates the full valve assembly 20 with a dc motor 71 and gear train (stator manifold removed). In this embodiment, as shown in FIG. 18, the stator seal housing 40 includes a mechanical stop 80 to enable a two-position valve configuration. However, the dc motor 71 may come equipped with any one of many rotary position sensor devices to command, sense and control multiple angular positions. The dc motor may also be assembled to a single gear train or multiple stacks of gear boxes.

Figure 16:
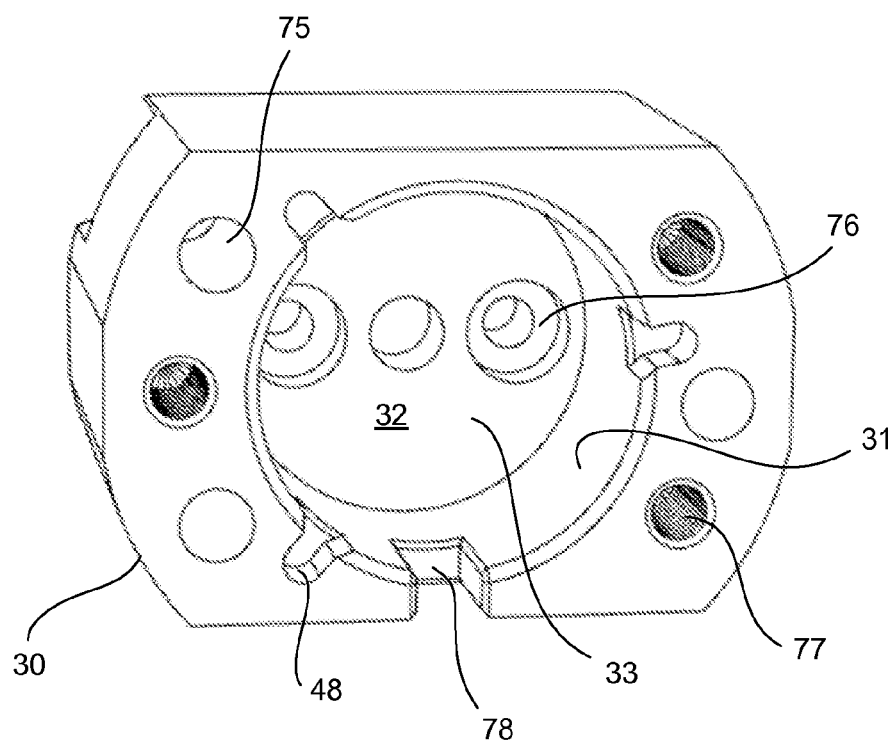
FIG. 16 is an enlarged, rear perspective view of the actuator housing of the alternative embodiment spring-less micro-fluidic valve assembly of FIG. 12.

Referring now to FIG. 16, a die cast actuator housing 30 is provided for the valve assembly 20 alternative embodiment of FIGS. 12-15. In this specific configuration, the inner wall 31 and the bearing support surface 33 are sized to provide support for the bearing assembly 38. In this configuration, the bearing assembly 38 is provided by a spherical thrust bearing, and thus, support surface 33 provides axial support for the base 67 of the thrust bearing.

Again, similarly, the inner wall 31 has a diameter tightly toleranced to align, and cooperatively receive portions of the stator seal housing 40 therein. In addition, clocking or angular alignment and positioning of the stator seal housing 40 with the actuator housing 30 is similarly accomplished using three slots 48 formed in the mating surface facing the seal housing.

The entire actuator housing 30 is electroless nickel plated for corrosion resistance or the part can be made of steel. Also included are thru holes 75 for mounting the actuator housing 30 to the stator seal housing 40, thru holes 76 for mounting the dc motor and threaded holes 77 for fastening the stator manifold device 45. Furthermore, a mechanical slot 78 is provided that is used for engaging a mechanical stop 80 on the stator seal housing 40 (FIG. 18).

Figure 14:
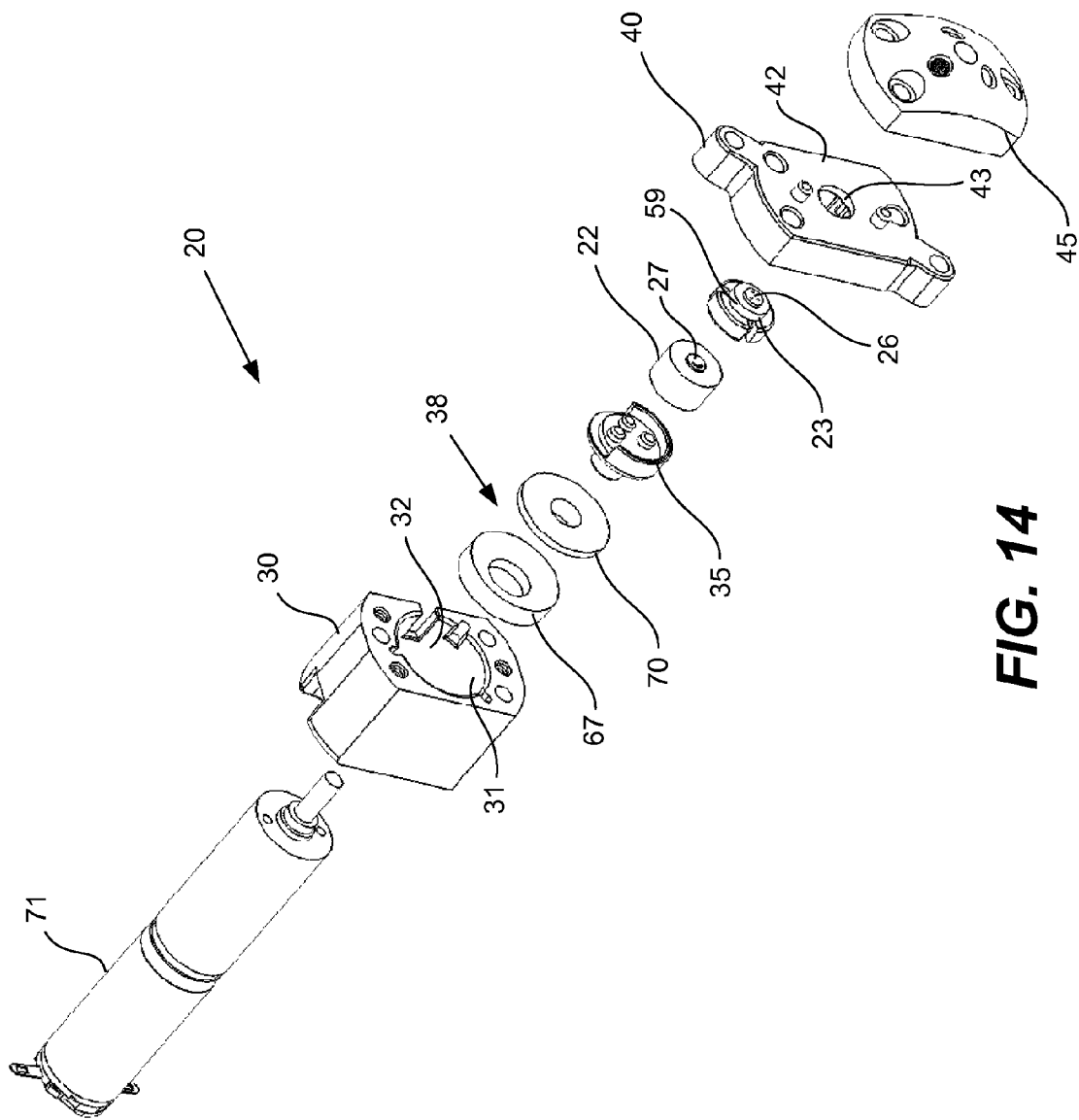
FIG. 14 is an exploded top perspective view of the alternative embodiment spring-less micro-fluidic valve assembly of FIG. 12.
Figure 15:
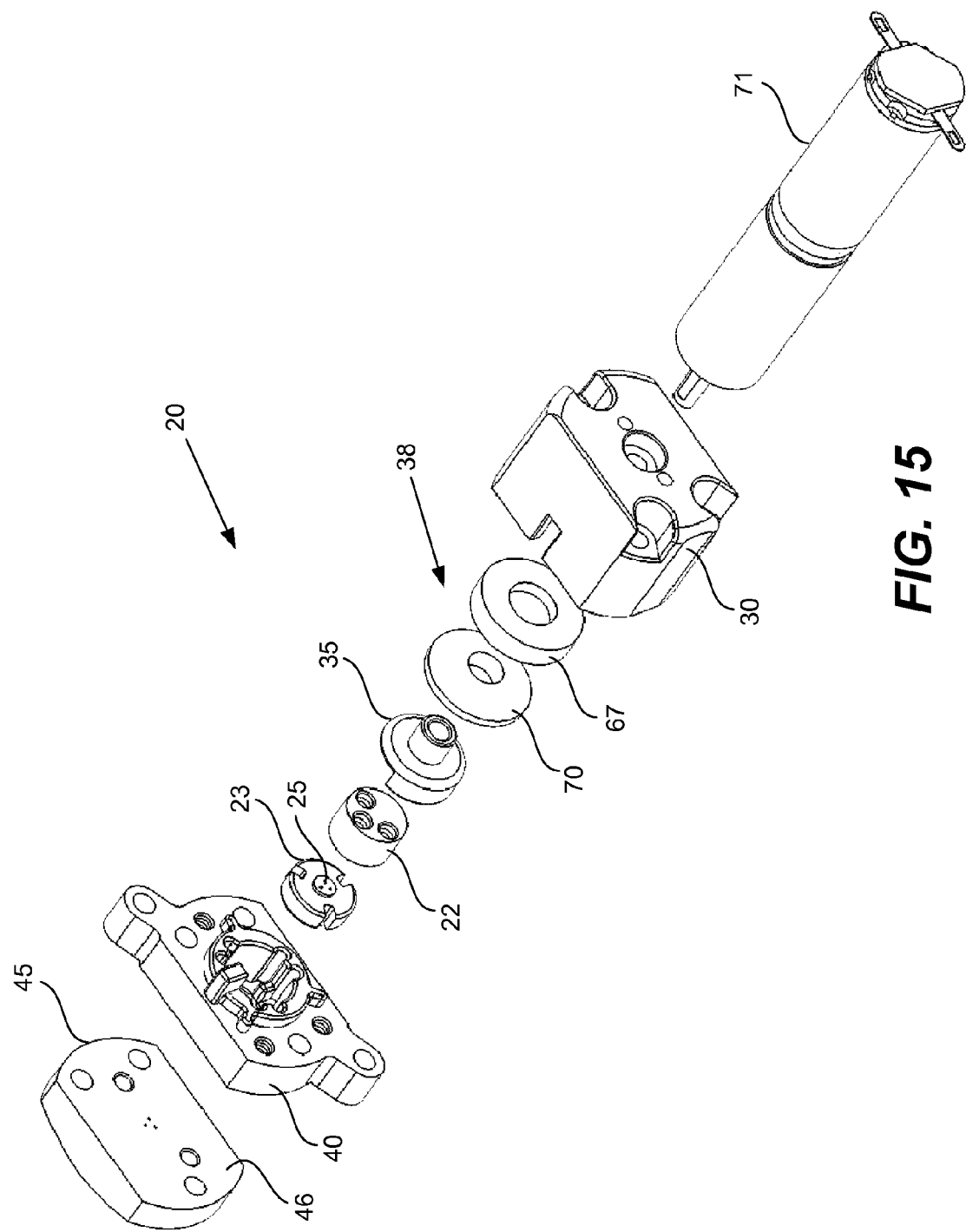
FIG. 15 is an exploded bottom perspective view of the alternative embodiment spring-less micro-fluidic valve assembly of FIG. 12.
Figure 17:
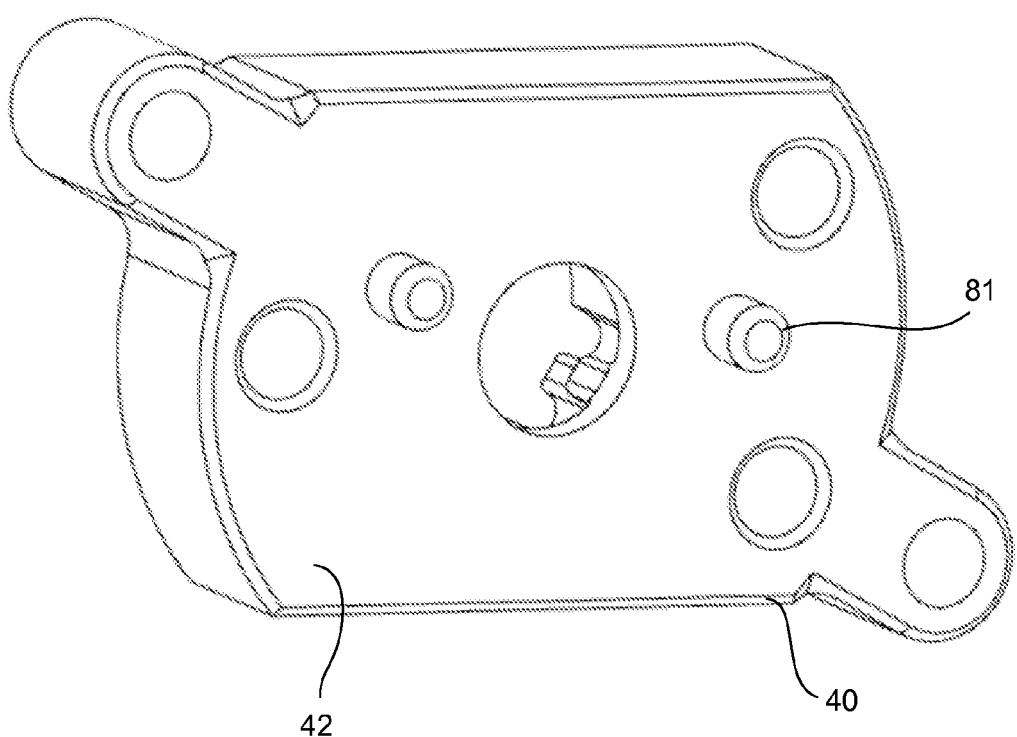
FIG. 17 is an enlarged, front perspective view of a stator seal housing of the alternative embodiment spring-less micro-fluidic valve assembly of FIG. 12.

Referring now to FIG. 17, a front side of the stator seal housing 40 is shown of the alternative embodiment valve assembly of FIGS. 12-15, illustrating cast-in alignment pins 81 for positioning and alignment of the stator manifold device 45 on the front side. FIG. 18 illustrates a backside of the stator seal housing 40 which includes the three alignment ribs 56 protruding outward from an alignment ring 79. The ribs 56 and outer diameter of the alignment ring 79 are tightly tolerance with the corresponding receiving slots 48 and the inner wall 31 of the actuator housing 30 (FIGS. 14 and 16). In addition, referring back to FIG. 18, the stator seal housing 40 includes three interior positioning ribs 57 for receipt in corresponding slots 61 in the stator seal device 23 for alignment thereof and an inside diameter for receipt and alignment of the stator seal outside diameter.

Figure 19:
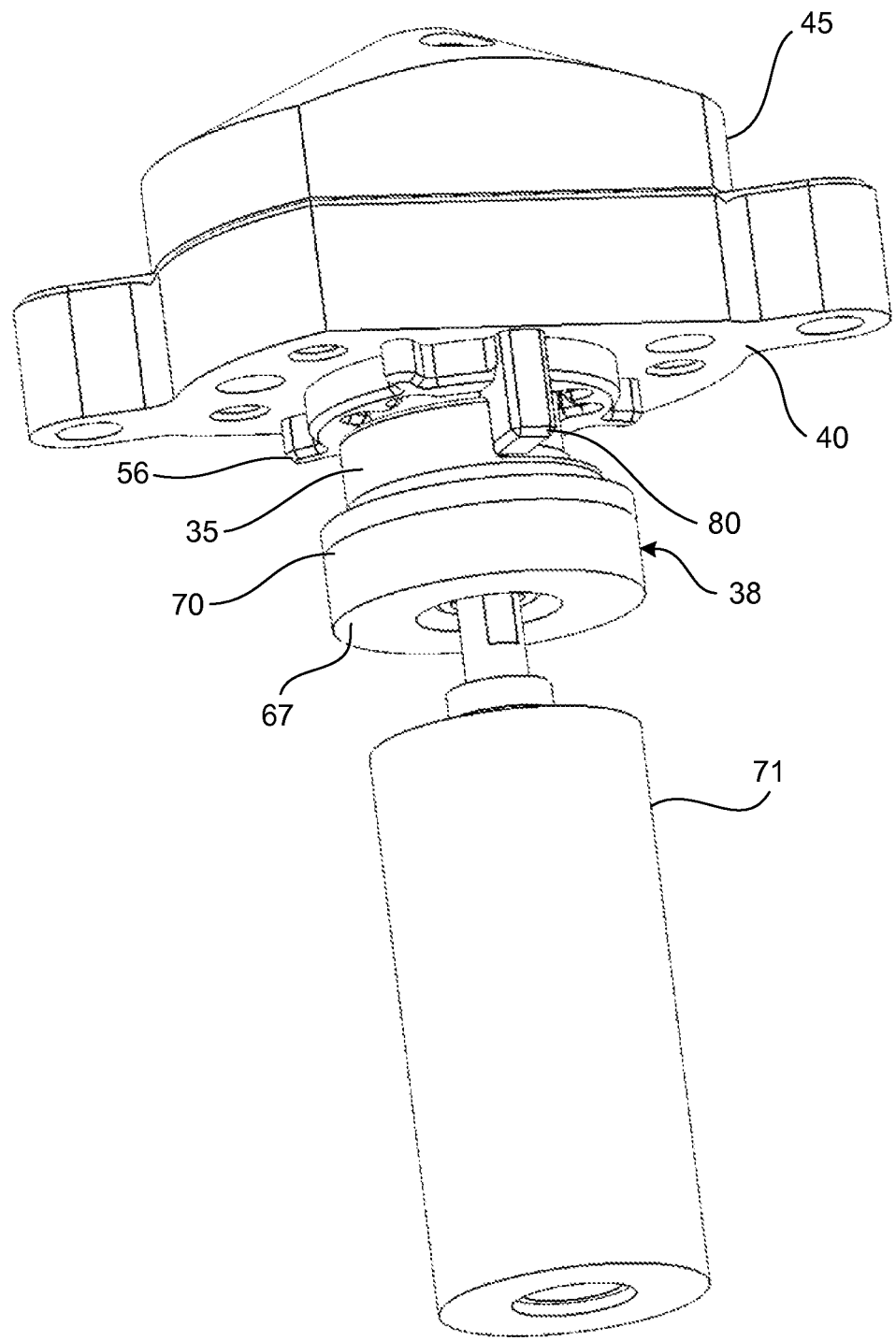
FIG. 19 is an enlarged, bottom perspective view of the alternative embodiment of the spring-less micro-fluidic valve assembly of FIG. 13, with the motor assembly and actuator housing removed.

If it is necessary to mount the valve from the back side to a manifold, two thru holes 82 are supplied on wing features. Threaded holes 85 are also available for mounting the actuator housing 30 to the stator seal housing 40. Furthermore, as shown in FIGS. 18 and 19, a mechanical hard stop 80 is provided that limits rotation of the shaft adapter 28, rotatably supporting the rotor seal device 22, in order to provide position fluid control. The entire die cast part is electroless nickel plated for corrosion resistance or can be made from steel.

Figure 20:
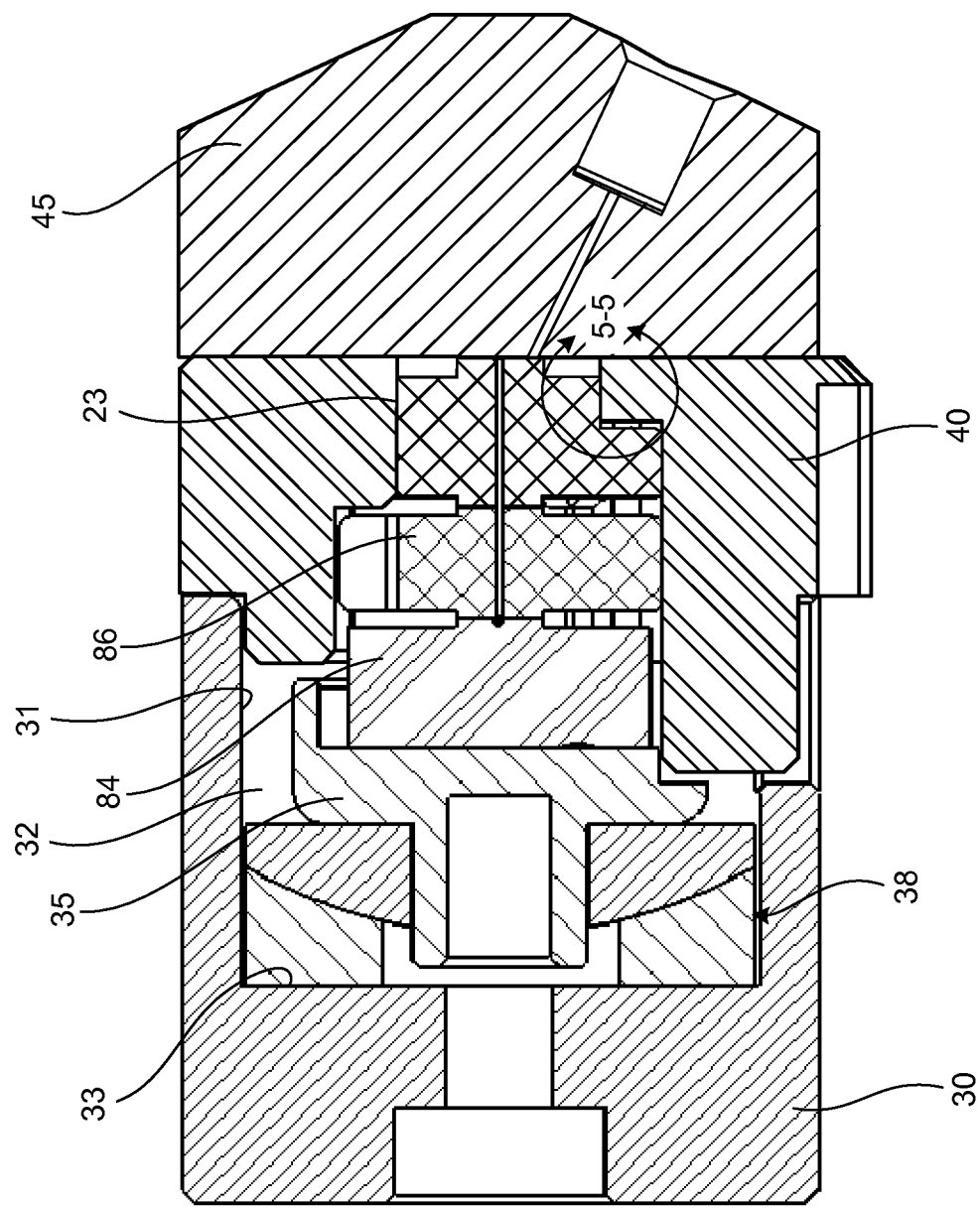
FIG. 20 is a side elevation view, in cross section, of another alternative embodiment of the spring-less micro-fluidic valve assembly of FIG. 1, having a ceramic rotor face seal component a ceramic stator face seal component sandwiched between polymer components thereof.
Figure 21:
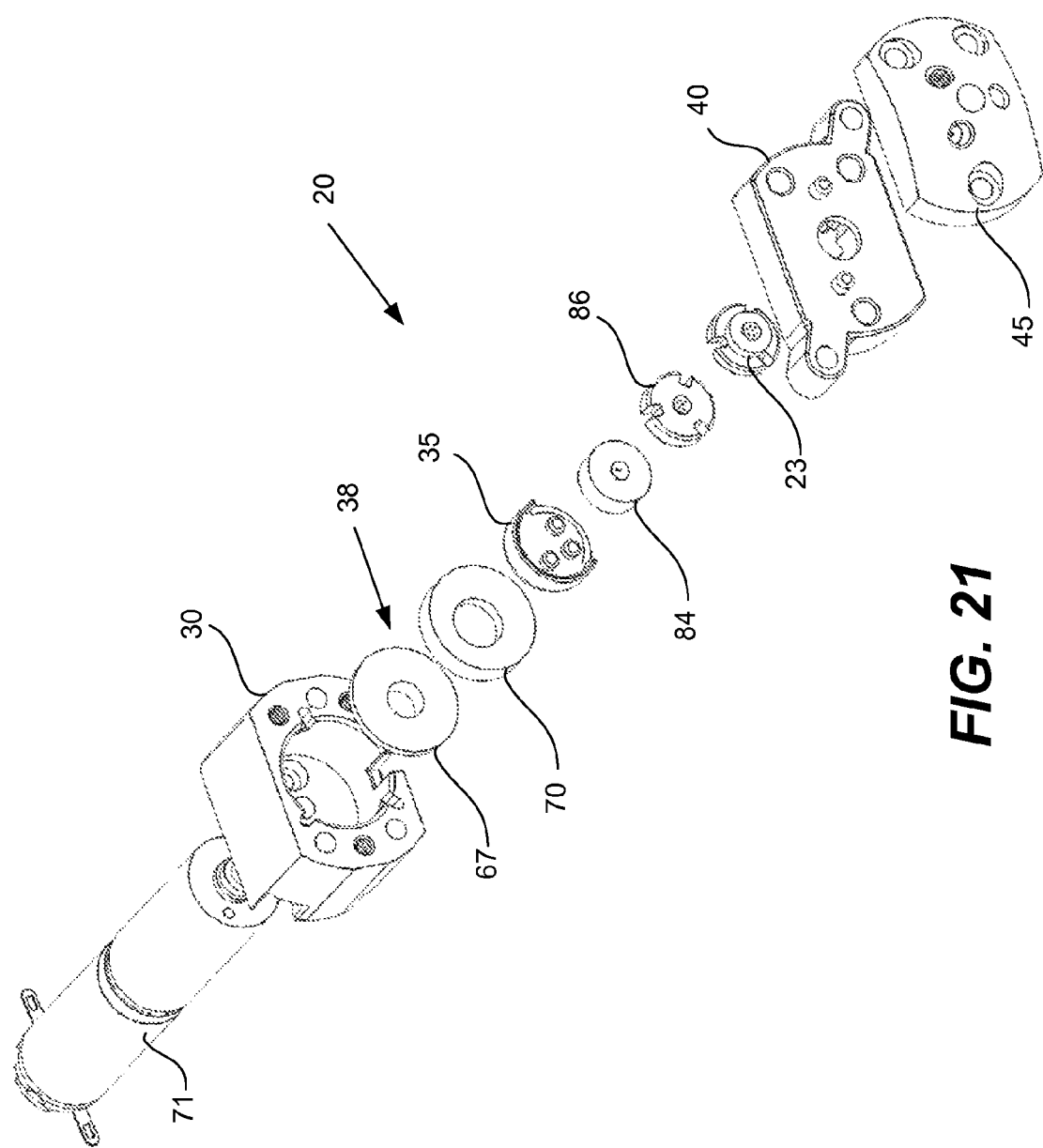
FIG. 21 is an exploded top perspective view of the alternative embodiment spring-less micro-fluidic valve assembly of FIG. 20, together with a drive motor assembly.
Figure 22:
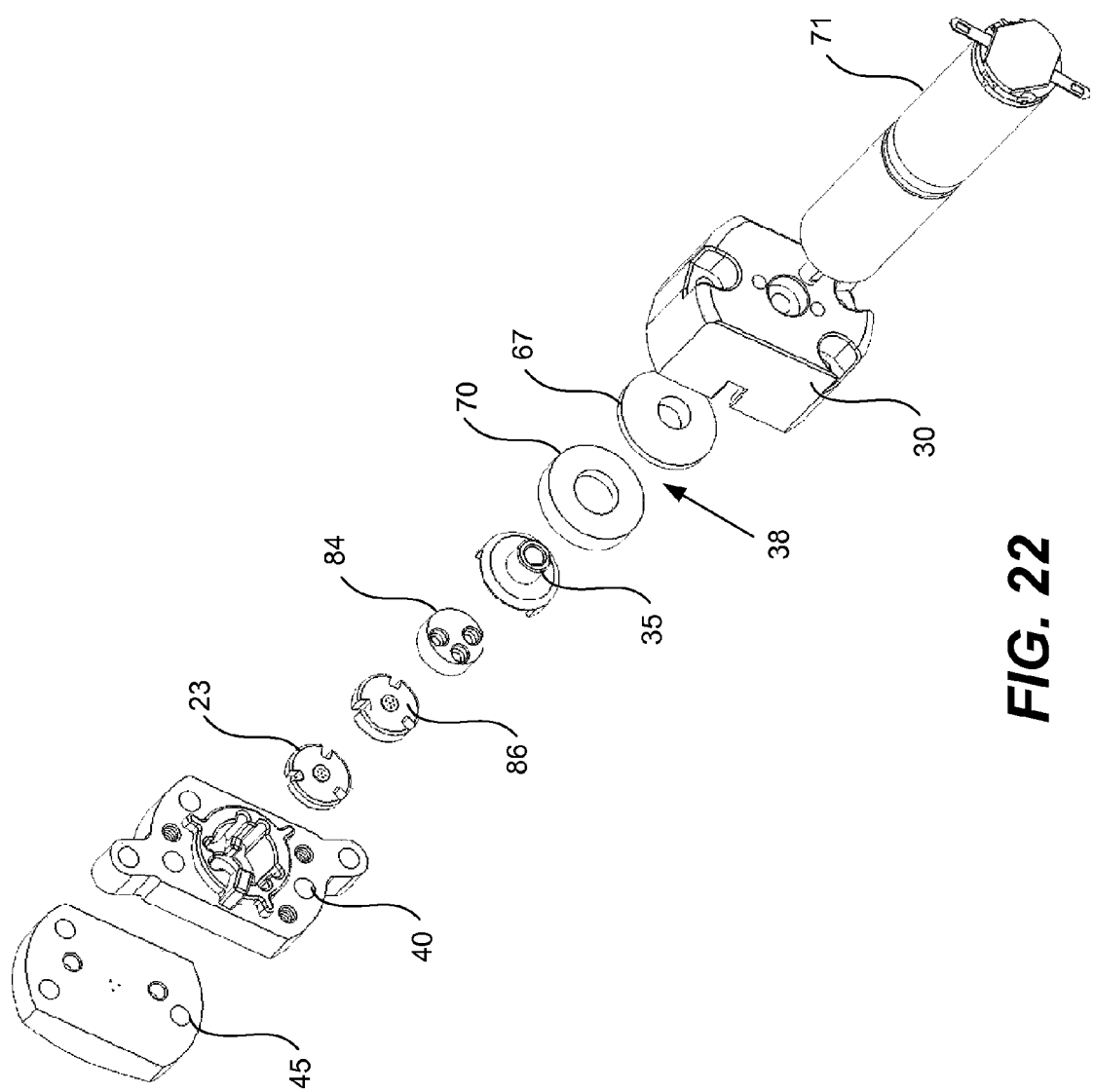
FIG. 22 is an exploded bottom perspective view of the alternative embodiment spring-less micro-fluidic valve assembly of FIG. 21.

Another specific configuration of the thrust bearing embodiment is shown in FIGS. 20-22. In this thrust bearing configuration of the bearing assembly 38, the valve assembly 20 includes a ceramic rotor seal device 22, a ceramic stator face seal 86 and polymer stator seal device 23. The ceramic rotor seal device 22 is supported by a shaft adapter 28 which sits atop a two part spherical thrust bearing 38 contained in the receiving passage 32 of actuator housing 30. A stator manifold device 45 is mounted to the stator seal housing 40 and contacts the stator contact surface 26 of the stator seal device 23.

In this variation of the invention the ceramic rotor seal device 84 and ceramic stator face seal 86 are sandwiched between a polymer spherical thrust bearing 38 and the polymer (PCTFE or similar material) stator seal device 23. The polymer combination functions to produce a spring effect while at the same time enables the hard ceramic surfaces of the rotor seal device 84 and the stator face seal 86 to be oriented substantially parallel to one another even though other components in the stack may have non-parallel surfaces in contact. A condition of non-parallelism between hard surfaces contributes to reduced life caused by uneven loading and wear of the surfaces. However, for this alternate design, the polymer spherical thrust bearing 38 and the polymer stator seal device 23 allow the hard coated ceramic rotor seal to rotate on the ceramic stator face seal in a more uniform motion as the bearing on one end and polymer seal on the other take up axial and planar misalignments. Again, FIGS. 5A and 5B applies to this design variation just as the initial embodiment where the stator face protrudes thousandths of an inch beyond the stator housing.

Figure 23:
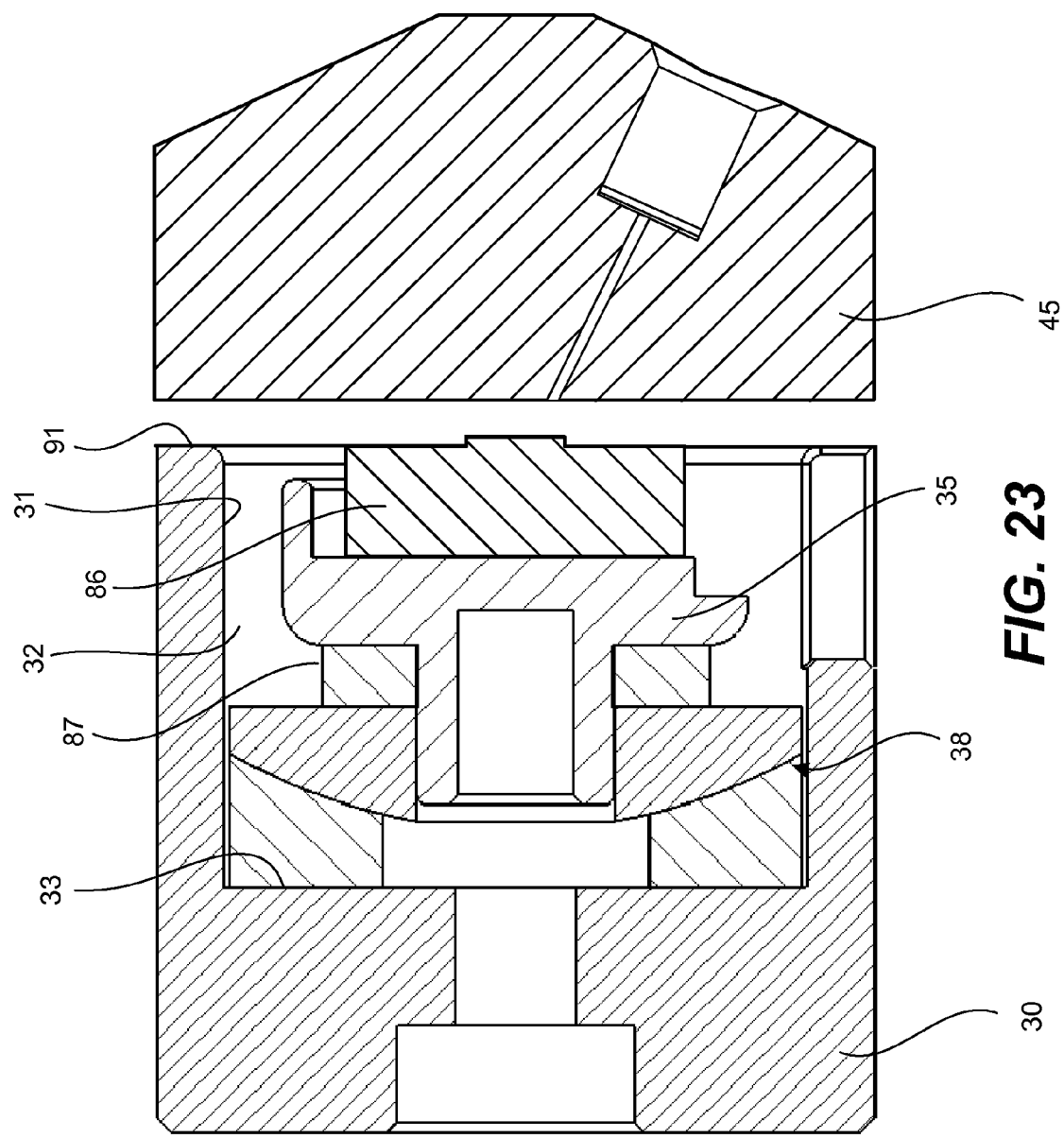
FIG. 23 is a side elevation view, in cross section, of another alternative embodiment of the spring-less micro-fluidic valve assembly of FIG. 1, having a ceramic rotor face seal component a ceramic stator face seal component sandwiched between polymer components thereof.
Figure 24:
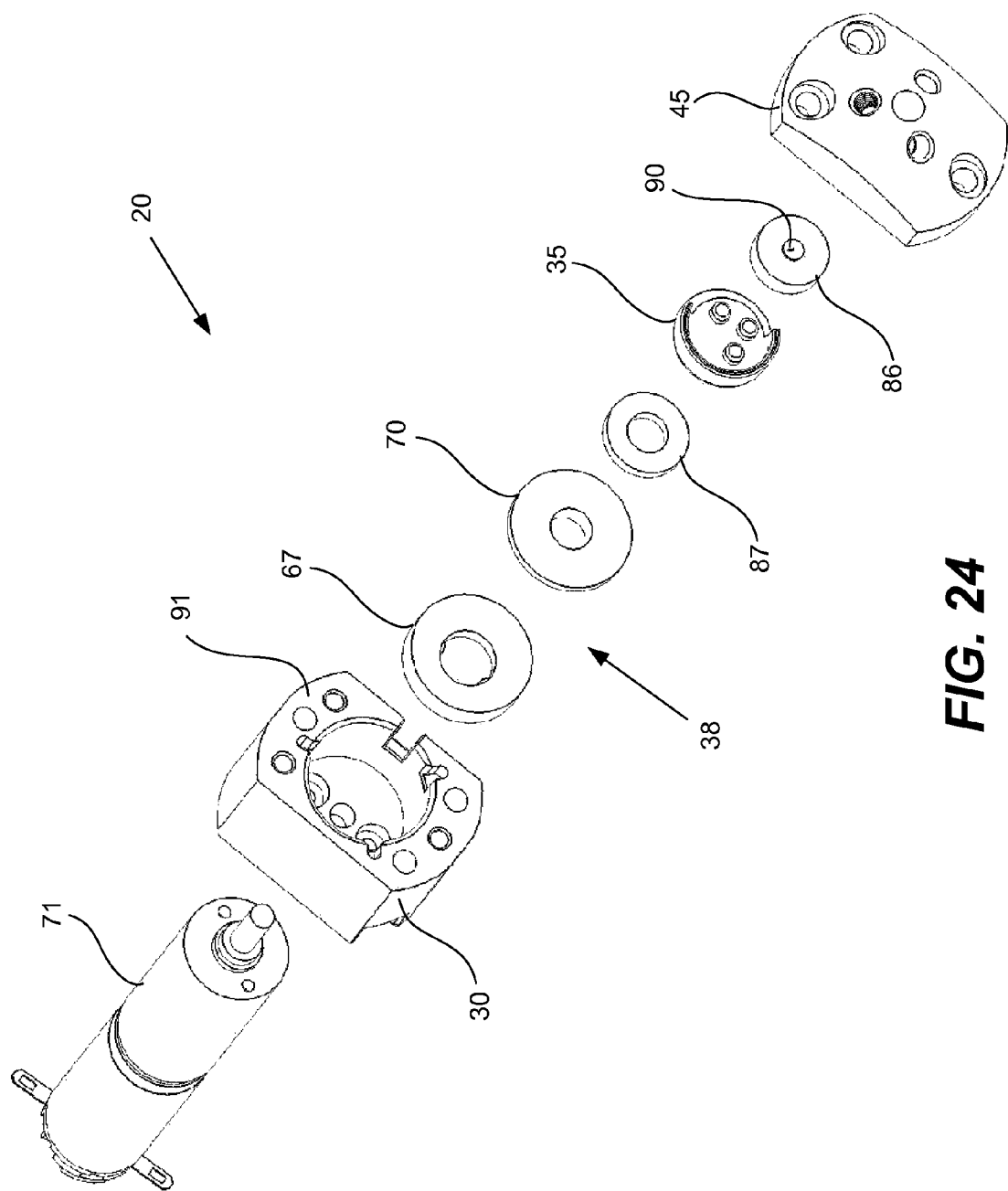
FIG. 24 is an exploded top perspective view of the alternative embodiment spring-less micro-fluidic valve assembly of FIG. 20, together with a drive motor assembly.
Figure 25:
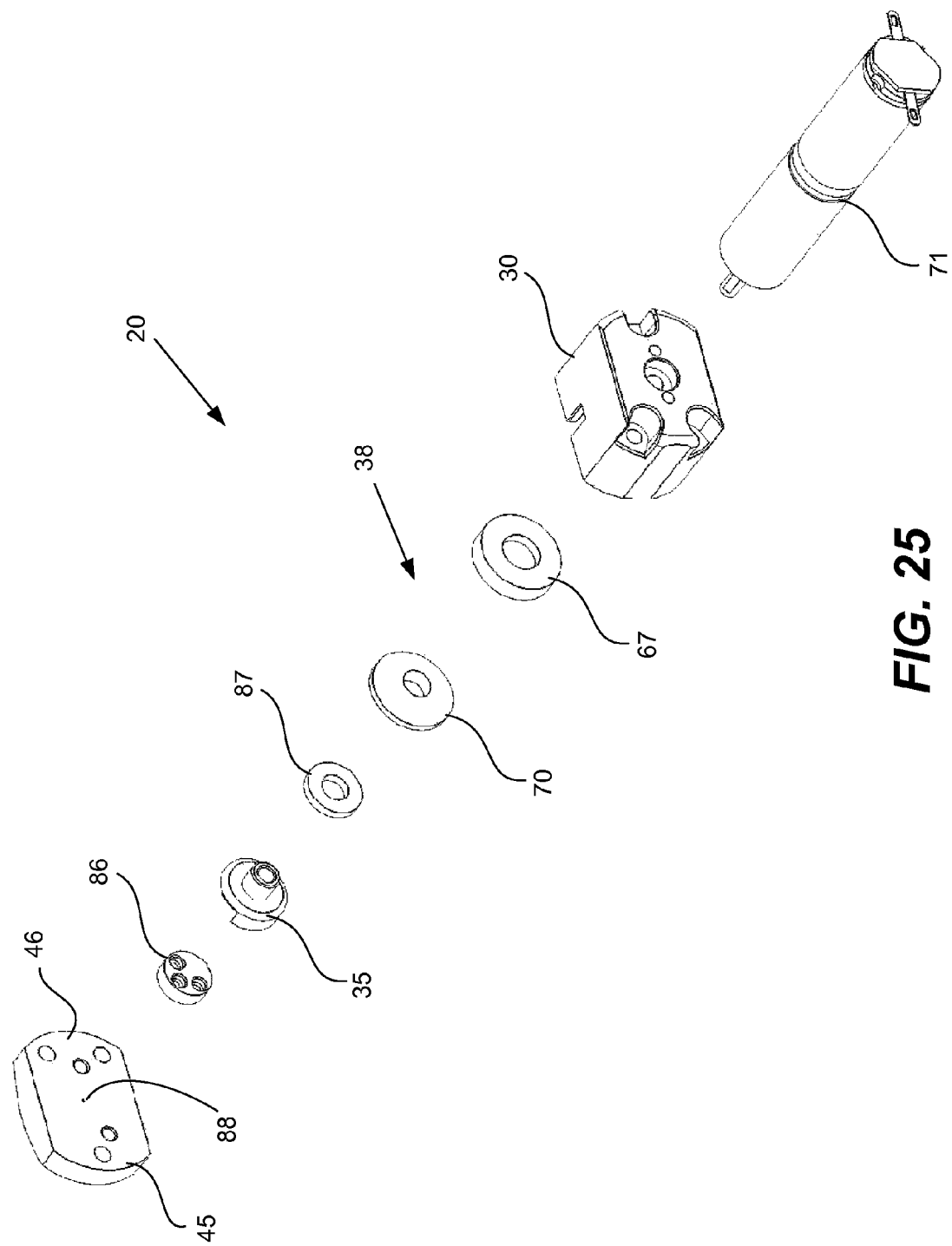
FIG. 25 is an exploded bottom perspective view of the alternative embodiment spring-less micro-fluidic valve assembly of FIG. 21.

Another variation of the present invention, shown in FIGS. 23-25, consists of addition of a polymer energizer 87 and ceramic rotor seal device 86. The rotor seal device is supported by a shaft adapter 28 which sits over the polymer energizer 87. A two part polymer spherical thrust bearing (i.e., bearing assembly 38) is inserted into the receiving passage 32, defined by the bearing support surface 33 and inner wall 31, of the actuator housing 30 to provide bearing support as well as contribute as a spring element. A stator manifold device 45 is mounted directly to the actuator housing 30, in this embodiment, eliminating the stator seal device and the stator seal housing of the previous embodiments. In this configuration, the substantially planar manifold contact surface 46 provides the stator face 88 that directly contacts the rotor face 90 of the coated ceramic rotor seal 86.

In this variation of the present invention, the flat washer-shaped polymer energizer 87 is comprised from PCTFE or other polymer material with stiffness in the range about 50 k lb/in to about 200 k lb/in. The polymer combination of polymer energizer 87 and polymer thrust bearing 38 cooperates to produce a spring effect while at the same time enables the face of the hard ceramic rotor 86 to be oriented substantially parallel with the metal surface or face of the stator manifold device 45 even though other components in the stack may have non-parallel surfaces in contact. A condition of non-parallelism between hard surfaces contributes to reduced life caused by uneven loading and wear of the surfaces. However, for this alternate design the polymer spherical bearing and polymer energizer allow the hard coated ceramic rotor seal to rotate on the coated metallic stator in a more uniform motion as the bearing and polymer energizer take up axial and planar misalignments. The concept of FIGS. 5A and 5B, applies to this design variation except in this configuration, it is the rotor face 90 of the rotor seal device 86 that protrudes the calibrated distance, $\delta$, beyond the substantially planar distal contacting surface 91 of the actuator housing 30.

Although the present invention has been primarily described as applying to shear face valve assemblies for applications below 2000 psi, and for pressure applications that require high lifecycle capabilities (e.g., such as all HPLC Instrument platforms/designs), it will be appreciated that this technology may be applied to all shear valve assembly platforms/designs (such as AI (analytical chemistry) and IVD (In-vitro Diagnostics)).

What is claimed is:

1. A spring-less micro-fluidic valve assembly comprising:
a stator seal device defining a substantially planar stator face and an opposite, distal facing stator contact surface perimetrically defined by a contact surface perimeter, said stator seal device including at least two or more stator channels extending therethrough from said contact surface to corresponding stator ports at said stator face;
a rotor seal device having a substantially planar rotor face defining one or more rotor channels and an opposite, proximally facing rotor contact surface;
a relatively rigid actuator housing having an inner wall defining an axially extending receiving passage therethrough, said inner wall including distally facing housing bearing support surface;
a shaft adapter configured for axial receipt in said receiving passage of the actuator housing, and defining a proximally facing adapter bearing support surface and a distally facing adapter contact surface configured for contact support of said rotor contact surface;
a bearing assembly disposed between the housing bearing support surface and the adapter bearing support surface for rotational support of the shaft adapter and rotor seal device thereof about a rotational axis;
a relatively rigid stator seal housing defining a stator passage formed and dimensioned for axial seated receipt of the stator seal device therein, and a distally facing housing contact surface that defines a receiving port extending into said stator passage, and is further formed and dimensioned for axial reciprocating receipt of said stator contact surface therethrough, the stator seal housing having a proximal portion configured to hard mount to a distal portion of said actuator housing, such that said actuator housing, said bearing assembly, said shaft adapter, said rotor seal device, said stator seal device and said stator seal housing collectively cooperate to axially position said contact surface of said stator seal device a substantially precise, calibrated distance, $\delta$, beyond said housing contact surface of the stator seal housing, in a non-leak-tight condition; and
a stator manifold device configured to mount to said stator seal housing, in a compressed mount condition, such that a proximally facing manifold contact surface of said manifold device contacts said stator contact surface, in the non-leak-tight condition, and repositions said stator contact surface, to a leak-tight condition, substantially flush with said housing contact surface, said stator seal device and said rotor seal device collectively being sufficiently compressed together at a compression pressure enabling leak-tight, relatively low pressure fluid flow between corresponding stator ports and at least one rotor channel at said rotor-stator interface therebetween.

2. The spring-less micro-fluidic valve assembly according to claim 1, wherein
said stator seal device is comprised of a polymer material.

3. The spring-less micro-fluidic valve assembly according to claim 2, wherein
said polymer material is Polyetherimide (PEI).

4. The spring-less micro-fluidic valve assembly according to claim 2, wherein
said rotor seal device is selected essentially from the group consisting of a polymer, a metallic and a ceramic material.

5. The spring-less micro-fluidic valve assembly according to claim 4, wherein
said stator seal housing and said actuator housing are comprised of a metallic material; and
said shaft adapter, said bearing assembly, and said stator manifold device are each comprised of one of a metallic material and a polymer material.

6. The spring-less micro-fluidic valve assembly according to claim 1, wherein
said stator seal device further including a mid section disposed between said stator face and said stator contact surface, said mid section having mid section perimeter wherein at least one portion thereof extends radially beyond that of contact surface perimeter, forming a distal facing stop surface therebetween.

7. The spring-less micro-fluidic valve assembly according to claim 1, wherein
said calibrated distance, δ, is in the range of about 0.001"+/−0.003" to about 0.015"+/−0.003".

8. The spring-less micro-fluidic valve assembly according to claim 7, wherein
said calibrated distance, δ, is in the range of about 0.008"+/−0.003".

9. The spring-less micro-fluidic valve assembly according to claim 7, wherein
said bearing assembly is selected essentially from the group consisting of a ball bearing assembly, a polymetric spherical bearing assembly and a thrust bearing assembly.

10. The spring-less micro-fluidic valve assembly according to claim 1, wherein
said distal facing stator contact surface of said stator seal device and the manifold contact surface are substantially planar and in a leak-tight relationship with one another.

11. The spring-less micro-fluidic valve assembly according to claim 10, wherein
said adapter contact surface of said shaft adapter and said contact surface of said rotor seal device are substantially planar and in rotationally locked together as a unit.

12. The spring-less micro-fluidic valve assembly according to claim 11, wherein
an alignment structure cooperatively aligns and rotationally locks said rotor seal device to said shaft adapter.

13. The spring-less micro-fluidic valve assembly according to claim 12, wherein
said alignment structure includes two or more corresponding guide pins extend distally from said adapter contact surface, and said contact surface of said rotor device define corresponding recesses for aligned receipt of the guide pins therein.

* * * * *